United States Patent
Dubhashi et al.

(10) Patent No.: US 11,864,904 B2
(45) Date of Patent: *Jan. 9, 2024

(54) SYSTEMS, DEVICES, AND METHODS FOR EVALUATING NEUROMODULATION THERAPY VIA DETECTION OF MAGNETIC FIELDS

(71) Applicant: Medtronic Ireland Manufacturing Unlimited Company, Dublin (IE)

(72) Inventors: Abhijeet Dubhashi, Cotati, CA (US); Douglas Hettrick, Andover, MN (US); Guo Xu, Santa Rosa, CA (US)

(73) Assignee: Medtronic Ireland Manufacturing Unlimited Company, Dublin (IE)

( * ) Notice: Subject to any disclaimer, the term of this patent is extended or adjusted under 35 U.S.C. 154(b) by 171 days.

This patent is subject to a terminal disclaimer.

(21) Appl. No.: 17/574,386

(22) Filed: Jan. 12, 2022

(65) Prior Publication Data
US 2022/0133210 A1 May 5, 2022

Related U.S. Application Data

(63) Continuation of application No. 15/959,004, filed on Apr. 20, 2018, now Pat. No. 11,253,189.

(Continued)

(51) Int. Cl.
| | | |
|---|---|---|
| *A61B 5/00* | (2006.01) |
| *A61B 18/14* | (2006.01) |
| *A61B 5/24* | (2021.01) |
| *A61B 5/242* | (2021.01) |
| *G01R 33/032* | (2006.01) |

(Continued)

(52) U.S. Cl.
CPC .............. *A61B 5/4052* (2013.01); *A61B 5/24* (2021.01); *A61B 5/242* (2021.01); *A61B 5/6857* (2013.01);

(Continued)

(58) Field of Classification Search
CPC . A61B 18/1492; A61B 18/18; A61B 18/1815; A61B 2017/320069; A61B 2018/0022; A61B 2018/00267; A61B 2018/00434; A61B 2018/00511; A61B 2018/00577; A61B 2018/00636; A61B 2018/00642; A61B 2018/0212; A61B 2018/1435; A61B 2018/1807; A61B 2090/3735; A61B 2090/376; A61B 2090/378; A61B 5/04001; A61B 5/04005;
(Continued)

(56) References Cited

U.S. PATENT DOCUMENTS

| | | | | |
|---|---|---|---|---|
| 2012/0277763 A1* | 11/2012 | Greenblatt | ............. | A61B 18/12 607/101 |
| 2014/0073903 A1* | 3/2014 | Weber | .................. | A61B 5/6852 606/34 |
| 2015/0201997 A1* | 7/2015 | Osypka | .............. | A61B 18/1492 606/41 |

* cited by examiner

*Primary Examiner* — Tigist S Demie
(74) *Attorney, Agent, or Firm* — Shumaker & Sieffert, P.A.

(57) ABSTRACT

Systems and methods for measuring the magnetic fields generated by renal nerves before and/or after neuromodulation therapy are disclosed herein. One method for measuring the magnetic field of target nerves during a neuromodulation procedure includes positioning a neuromodulation catheter at a target site within a renal blood vessel of a human patient near the target nerves, and detecting a measurement of the magnetic field generated by the target nerves. The method can further include determining, based on the measurement of the magnetic field, a location of the target nerves, a location of ablation at the target nerves, and/or a percentage the target nerves were ablated by delivered neuromodulation energy.

20 Claims, 13 Drawing Sheets

Related U.S. Application Data

(60) Provisional application No. 62/622,037, filed on Jan. 25, 2018, provisional application No. 62/621,345, filed on Jan. 24, 2018.

(51) Int. Cl.
  *A61B 18/00* (2006.01)
  *A61B 18/18* (2006.01)
  *G01R 33/26* (2006.01)
  *A61B 90/00* (2016.01)
  *A61B 18/02* (2006.01)
  *A61B 17/32* (2006.01)

(52) U.S. Cl.
  CPC ........ *A61B 18/1492* (2013.01); *G01R 33/032* (2013.01); *A61B 18/18* (2013.01); *A61B 18/1815* (2013.01); *A61B 2017/320069* (2017.08); *A61B 2018/0022* (2013.01); *A61B 2018/00267* (2013.01); *A61B 2018/00434* (2013.01); *A61B 2018/00511* (2013.01); *A61B 2018/00577* (2013.01); *A61B 2018/00636* (2013.01); *A61B 2018/00642* (2013.01); *A61B 2018/0212* (2013.01); *A61B 2018/1435* (2013.01); *A61B 2018/1807* (2013.01); *A61B 2090/376* (2016.02); *A61B 2090/378* (2016.02); *A61B 2090/3735* (2016.02); *G01R 33/26* (2013.01)

(58) Field of Classification Search
  CPC .. A61B 5/4052; A61B 5/6857; G01R 33/032; G01R 33/26
  See application file for complete search history.

SYSTEMS, DEVICES, AND METHODS FOR EVALUATING NEUROMODULATION THERAPY VIA DETECTION OF MAGNETIC FIELDS

CROSS-REFERENCE TO RELATED APPLICATIONS

The present application is a continuation of U.S. patent application Ser. No. 15/959,004, filed Apr. 20, 2018, and entitled, "SYSTEMS, DEVICES, AND METHODS FOR EVALUATING NEUROMODULATION THERAPY VIA DETECTION OF MAGNETIC FIELDS," which claims the benefit of U.S. Provisional Patent Application No. 62/621,345, filed Jan. 24, 2018, and U.S. Provisional Patent Application No. 62/622,037, filed Jan. 25, 2018, each of which are incorporated herein by reference in their entirety.

TECHNICAL FIELD

The present technology is related to neuromodulation. In particular, various embodiments of the present technology are related to systems and methods for measuring magnetic fields generated by renal nerves before and/or after neuromodulation therapy.

BACKGROUND

The sympathetic nervous system (SNS) is a primarily involuntary bodily control system typically associated with stress responses. Fibers of the SNS extend through tissue in almost every organ system of the human body and can affect characteristics such as pupil diameter, gut motility, and urinary output. Such regulation can have adaptive utility in maintaining homeostasis or in preparing the body for rapid response to environmental factors. Chronic over-activation of the SNS, however, is a common maladaptive response that can drive the progression of many disease states. Excessive activation of the renal SNS in particular has been identified experimentally and in humans as a likely contributor to the complex pathophysiology of arrhythmias, hypertension, states of volume overload (e.g., heart failure), and progressive renal disease.

Sympathetic nerves of the kidneys terminate in the renal blood vessels, the juxtaglomerular apparatus, and the renal tubules, among other structures. Stimulation of the renal sympathetic nerves can cause, for example, increased renin release, increased sodium reabsorption, and reduced renal blood flow. These and other neural-regulated components of renal function are considerably stimulated in disease states characterized by heightened sympathetic tone. For example, reduced renal blood flow and glomerular filtration rate as a result of renal sympathetic efferent stimulation is likely a cornerstone of the loss of renal function in cardio-renal syndrome, (i.e., renal dysfunction as a progressive complication of chronic heart failure). Pharmacologic strategies to thwart the consequences of renal sympathetic stimulation include centrally-acting sympatholytic drugs, beta blockers (e.g., to reduce renin release), angiotensin-converting enzyme inhibitors and receptor blockers (e.g., to block the action of angiotensin II and aldosterone activation consequent to renin release), and diuretics (e.g., to counter the renal sympathetic mediated sodium and water retention). These pharmacologic strategies, however, have significant limitations including limited efficacy, compliance issues, side effects, and others.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present technology.

DETAILED DESCRIPTION

Figure 1A:
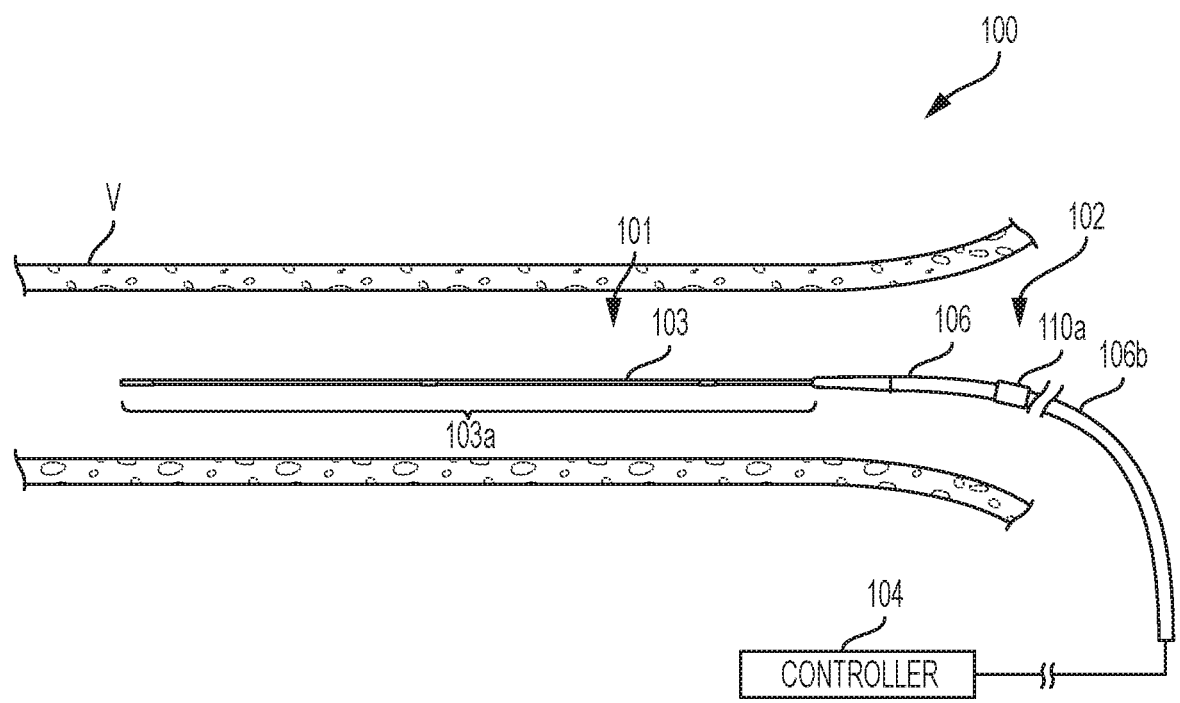
FIG. 1A is a partially schematic side view of a neuromodulation system with a distal portion of a guidewire positioned within a blood vessel of a human patient and configured in accordance with embodiments of the present technology.

Systems and methods in accordance with embodiments of the present technology are directed to measuring magnetic fields generated by electrical signals propagating along one or more nerves near a blood vessel before, during, and/or after a neuromodulation procedure. Conventional techniques for measuring the very small (e.g., nanoscale) electrical signals and/or magnetic fields associated with nerves inside a human patient include, for example, super-cooled magnetometers (e.g., cryogenically-cooled superconducting quantum interference ("SQUID") devices). However, such devices are expensive, bulky, and difficult if not impossible to position intravascularly within a patient.

In contrast with conventional techniques, in several of the embodiments described below, a neuromodulation system can include an optical magnetic sensor configured to be positioned intravascularly within a blood vessel (e.g., a renal artery) of a human patient, and proximate to (e.g., integrated with) a neuromodulation catheter configured to deliver neuromodulation energy to target nerves at or adjacent to a target site within the blood vessel. The optical magnetic sensor can measure the magnetic field ("the neural magnetic field") generated by electricals signals (e.g., action potentials) propagating through the target nerves. In some embodiments, for example, the neuromodulation system includes a magnet assembly configured to generate a variable magnetic field for amplifying and/or enhancing the neural magnetic field to improve the detectability of the neural magnetic field. A controller can receive measurements of the neural magnetic field from the optical magnetic sensor and process the measurements to, for example, determine a location of ablation(s) along the target nerves, trace or map the target nerves, determine a percentage reduction or proportional reduction in neural activity as a result of neuromodulation energy delivered to the target nerves, determine a temporal shape of the corresponding electrical signals, etc. Accordingly, systems configured in accordance with the present technology are expected to improve the efficacy of neuromodulation procedures by providing additional information useful for evaluating the neuromodulation procedure.

In a particular embodiment of the present technology, a neuromodulation system can measure the magnetic field generated by renal nerves surrounding a renal blood vessel before and/or after a renal denervation procedure is performed in the renal blood vessel. The pre-procedure magnetic field measurements, the post-procedure magnetic field measurements, and/or a comparison of the pre- and post-procedure magnetic field measurements can be used to detect the location of ablations on the renal nerves and/or to determine a percentage reduction in renal neural activity (e.g., a percentage of ablation) as a result of the renal denervation procedure.

Specific details of several embodiments of the present technology are described herein with reference to FIGS. 1A-15. Although many of the embodiments are described with respect to devices, systems, and methods for intravascular renal neuromodulation, other applications and other embodiments in addition to those described herein are within the scope of the present technology. For example, at least some embodiments of the present technology may be useful for extravascular neuromodulation, intravascular non-renal neuromodulation, and/or use in therapies other than neuromodulation. It should be noted that other embodiments in addition to those disclosed herein are within the scope of the present technology. Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology.

As used herein, the terms "distal" and "proximal" define a position or direction with respect to a clinician or a clinician's control device (e.g., a handle of a neuromodulation catheter). The terms, "distal" and "distally" refer to a position distant from or in a direction away from a clinician or a clinician's control device along the length of device. The terms "proximal" and "proximally" refer to a position near or in a direction toward a clinician or a clinician's control device along the length of device. The headings provided herein are for convenience only and should not be construed as limiting the subject matter disclosed.

I. SELECTED EMBODIMENTS OF NEUROMODULATION CATHETERS AND SYSTEMS

Figure 1B:
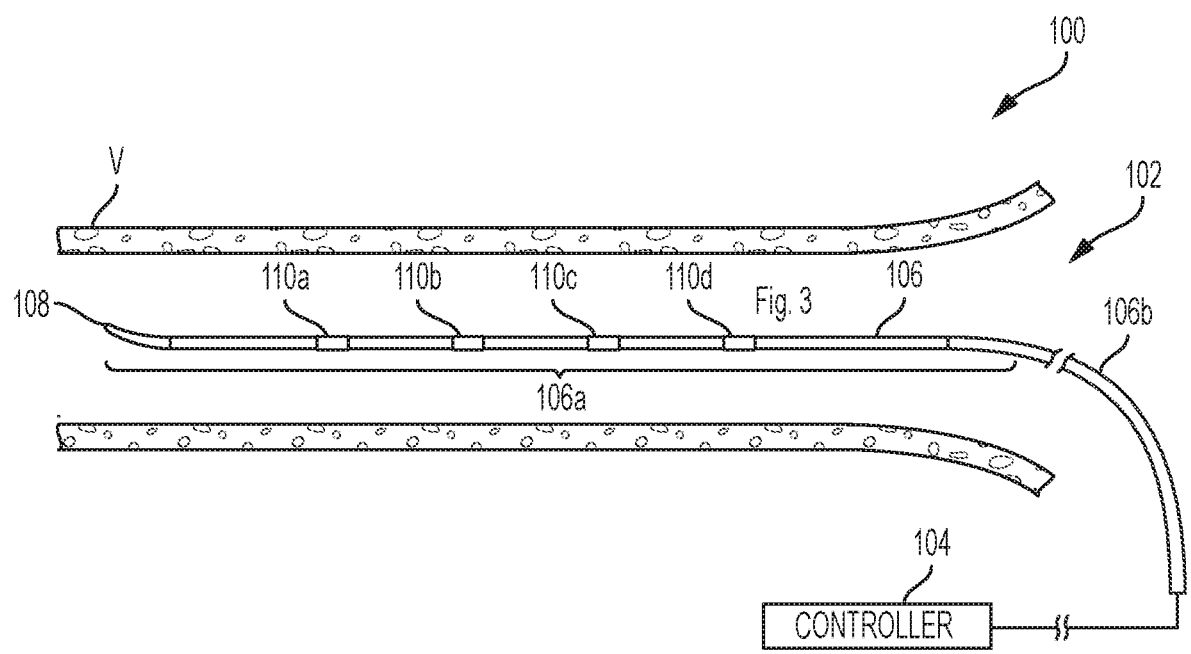
FIGS. 1B and 1C are partially schematic side views of the neuromodulation system shown in FIG. 1A with a distal portion of a neuromodulation catheter in a first state and a second state, respectively, within the blood vessel of the human patient in accordance with embodiments of the present technology.
Figure 1C:
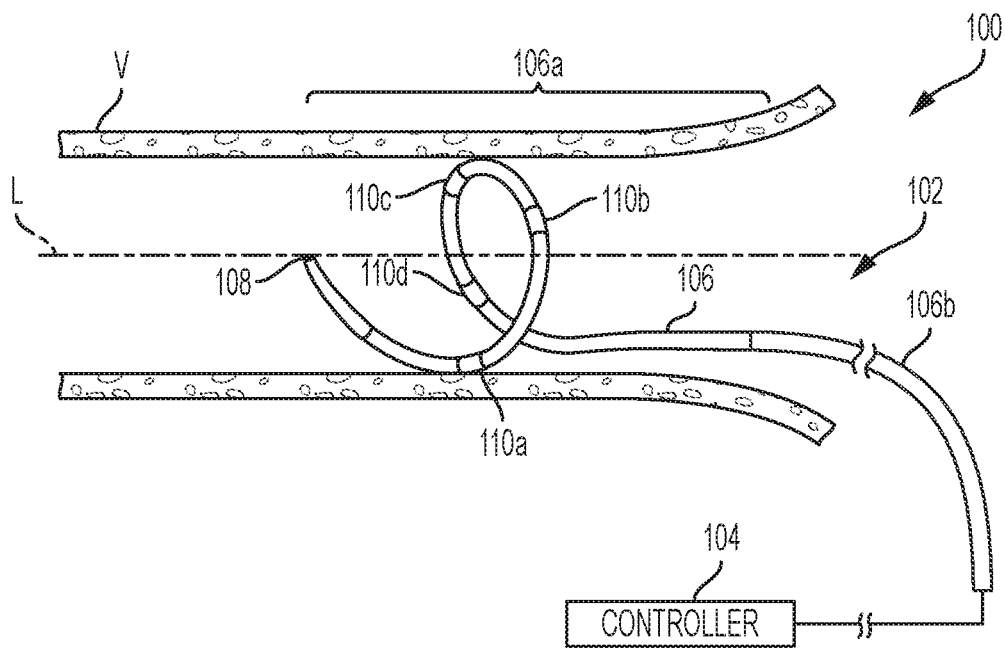

FIGS. 1A-1C are partially schematic side views of a neuromodulation system 100 configured in accordance with an embodiment of the present technology and shown in different arrangements while positioned at a target site within a blood vessel V (e.g., a renal artery) of a human patient. The neuromodulation system 100 includes a guidewire 101 (only visible in FIG. 1A) and a neuromodulation catheter 102 that can be advanced over the guidewire 101 to the target site within the blood vessel V. In other embodiments, the neuromodulation catheter 102 can be configured for delivery to the target site via other methods (e.g., via a guide catheter, via sheath retraction, via a pull-wire, etc.). The neuromodulation catheter 102 is configured to perform neuromodulation therapy at the target site to, for example, ablate nerves proximate the wall of the blood vessel V. The neuromodulation system 100 further includes one or more controllers 104 communicatively coupled to the neuromodulation catheter 102 via a wired or wireless communication link. As discussed in greater detail below, in certain embodiments, the neuromodulation catheter 102 can further include an (i) optical magnetic sensor configured to detect the magnetic field(s) generated by tire nerves proximate the wall of the blood vessel V and/or (ii) a magnet assembly or amplifying and/or enhancing the magnetic field(s).

Referring to FIG. 1A, the guidewire 101 includes an elongated member 103 having a distal portion 103a configured to be positioned at the target site within the blood vessel V and a proximal portion 103b (illustrated in FIG. 4A) that extends outside of the patient to a handle 111 (also illustrated in FIG. 4A) or other feature(s) that allow an operator to manipulate the distal portion 103a to the desired position/orientation. The elongated member 103 can be sized to be slidably positioned within a lumen of the neuromodulation catheter 102. Additionally, the elongated member 103 can have a uniform stiffness along its length, or can have a stiffness that varies along its length. In other embodiments, the elongated member 103 may comprise other suitable components and/or configurations.

As best shown in FIG. 1B, the neuromodulation catheter 102 includes an elongated shaft 106 configured to be slidably delivered over the guidewire 101. The elongated shaft 106 has a distal portion 106a configured to be intravascularly positioned at the target site within the blood vessel V and a proximal portion 106b extending outside of the patient to the handle 111 (FIG. 4A) or other features that allow an operator to manipulate the distal portion 106a of the elongated shaft 106. As shown in FIGS. 1B and 1C, for example, the neuromodulation catheter 102 is transformable between a first state or arrangement in which the distal portion 106a of the elongated shaft 106 is at least generally straight (FIG. 1B), and a second (e.g., deployed, expanded, etc.) state or arrangement in which the distal portion 106a is transformed or otherwise expanded to a spiral/helical shape (FIG. 1C).

Referring to FIGS. 1B and 1C together, the neuromodulation catheter 102 includes a plurality of energy delivery elements, such as electrodes 110, spaced along the distal portion 106a of the elongated shaft 106 and a distal tip 108 (e.g., an atraumatic tip). In the illustrated embodiment, the neuromodulation catheter 102 includes four electrodes 110 (identified individually as first through fourth electrodes 110a-110d, respectively). In other embodiments, however, the neuromodulation catheter 102 may include one, two, three, or more than four electrodes 110, and/or may include different energy delivery elements. The electrodes 110 are configured to deliver neuromodulation energy to the target site to modulate or ablate nerves (e.g., renal nerves) proximate to the target site. In other embodiments, the neuromodulation catheter 102 can include electrodes, transducers, or other elements to deliver energy to modulate nerves using other suitable neuromodulation modalities, such as pulsed electrical energy, microwave energy, optical energy, ultrasound energy (e.g., intravascularly delivered ultrasound and/or high-intensity focused ultrasound ("HIFU")), direct heat energy, radiation (e.g., infrared, visible, and/or gamma radiation), and/or other suitable types of energy.

The dimensions (e.g., outer diameter and length) of the distal portion 106a of the elongated shaft 106 (e.g., the portion that takes on the spiral/helical shape in the second state illustrated in FIG. 1C) can be selected to accommodate the vessels or other body lumens in which the distal portion 106a is designed to be delivered. For example, when in the second state, the axial length of the distal portion 106a of the elongated shaft 106 may be selected to be no longer than a patient's renal artery (e.g., typically less than 7 cm), and have a diameter that accommodates the inner diameter of a typical renal artery (e.g., about 2-10 mm). In other embodiments, the distal portion 106a of the elongated shaft 106 can have other dimensions depending on the body lumen within which it is configured to be deployed. In further embodiments, the distal portion 106a of the elongated shaft 106 can have other suitable shapes (e.g., semi-circular, curved, straight, etc.), and/or the neuromodulation catheter 102 can include multiple support members configured to carry one or more electrodes 110. The distal portion 106a of the elongated shaft 106 may also be designed to apply a desired outward radial force to a vessel when expanded to the spiral/helical second state to place one or more of the electrodes 110 in contact with the vessel wall.

In some embodiments, the neuromodulation system 100 includes a console (not shown). The controller 104 may be separated from the console or may be integrated with the console. The controller 104 can be configured to initiate, terminate, and/or adjust operation of one or more components (e.g., the electrodes 110, the optical magnetic sensor, the magnet assembly, etc.) of the neuromodulation catheter 102 directly and/or via the console. For example, as described in greater detail below, the controller 104 may be configured to initiate and receive measurements from the optical magnetic sensor. The console can be configured to communicate with the neuromodulation catheter 102 via a wireless and/or wired communication link. For example, in some embodiments the console can include an access port for receiving a wired connection to the neuromodulation catheter 102. The console can be configured to control, monitor, supply, and/or otherwise support operation of the neuromodulation catheter 102. The console can further be configured to generate a selected form and/or magnitude of energy for delivery to tissue at the target site via the electrodes 110, and therefore the console may have different configurations depending on the treatment modality of the neuromodulation catheter 102. For example, the console can include an energy generator (not shown) configured to generate RF energy. Further, the console can be configured to provide feedback to an operator before, during, and/or after a neuromodulation procedure such as, for example, a determined percentage (e.g., proportional) reduction in the magnetic field generated by targeted renal nerves.

Although the embodiment of the neuromodulation catheter 102 shown in FIGS. 1A-1C has a spiral/helically-shaped configuration, in other embodiments, the neuromodulation catheter 102 can have other suitable shapes, sizes, and/or configurations. Other suitable devices and technologies are described in, for example, U.S. Pat. Nos. 8,777,942; 9,084,610; 9,060,755; 8,998,894; PCT Application No. PCT/US2011/057754, filed Oct. 25, 2011; and U.S. Pat. No. 8,888,773. All of the foregoing applications are incorporated herein by reference in their entireties. One non-limiting example of a device and system includes the Simplicity Spyral™ multielectrode RF ablation catheter.

II. SELECTED EMBODIMENTS OF NEUROMODULATION SYSTEMS HAVING OPTICAL MAGNETIC SENSORS

The neuromodulation system 100 of the present technology includes at least one optical magnetic sensor configured to detect the very small magnetic field(s) ("the neural magnetic field") generated by electrical signals propagating through one or more nerves located near the wall of the blood vessel V ("the target nerves") before, during, and/or after delivery of neuromodulation energy using the neuromodulation catheter 102. In some embodiments, the optical magnetic sensor need not be cooled—for example, cryogenically-cooled to superconducting temperatures—and can instead operate at room or body temperature.

Figure 2:
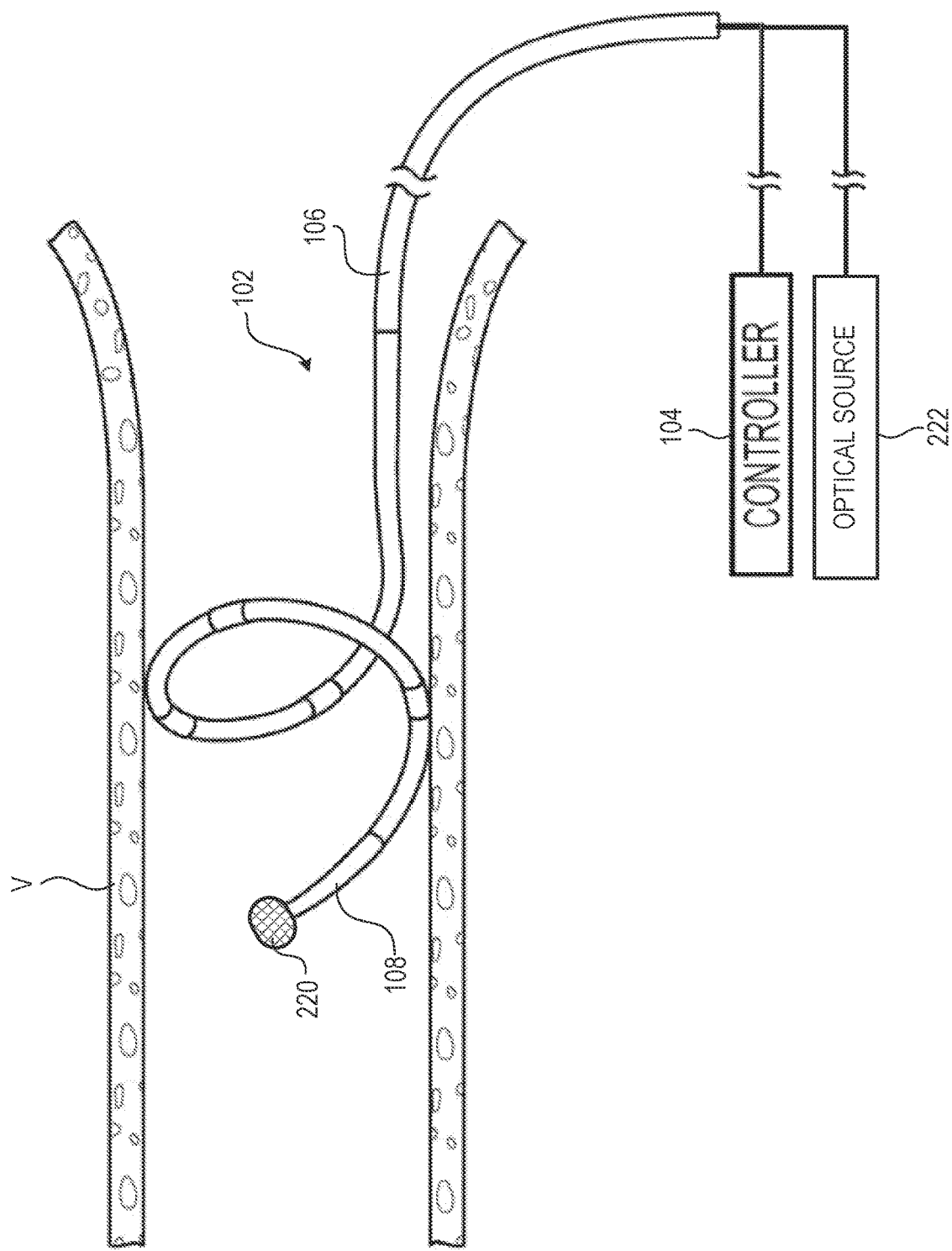
FIG. 2 is a partially schematic side view of the neuromodulation system shown in FIG. 1C with an optical magnetic sensor configured in accordance with embodiments of the present technology.

In certain embodiments, the optical magnetic sensor can be integrated with the neuromodulation catheter 102. FIG. 2, for example, is a partially schematic side view of the neuromodulation system 100 including an optical magnetic sensor 220 configured in accordance with embodiments of the present technology. In the illustrated embodiment, the optical magnetic sensor 220 extends distally from the distal tip 108 of the neuromodulation catheter 102. In other embodiments, the optical magnetic sensor 220 can be positioned differently with respect to the neuromodulation catheter 102 (e.g., positioned proximal to the distal tip 108). The optical magnetic sensor 220 can be coupled to an optical source (e.g., a laser light source) 222 via one or more optical fibers (not shown) extending, for example, through a lumen of the elongated shaft 106 of the neuromodulation catheter 102. As shown, the optical source 222 is positioned external to the neuromodulation catheter 102. In other embodiments, however, the optical source 222 may be positioned within the neuromodulation catheter 102 (e.g., positioned within the distal tip 108). In some embodiments, the optical magnetic sensor 220 can include a transparent (e.g., glass) chamber optically coupled to the optical source 222 and including cesium in a gaseous state. The magnetic moment (spin) of the cesium atoms in the chamber is affected by the neural magnetic field, therefore enabling the optical magnetic sensor to operate as a magnetometer for detecting properties of the neural magnetic field and the associated neural electrical signals.

More specifically, to detect the neural magnetic field based on its effect on the cesium atoms, the optical magnetic sensor 220 can further include a detection element for detecting a component of the optical signal after it passes through the chamber. The detection element can be operatively coupled to the controller 104 and configured to communicate detected measurements of the optical signal to the controller 104. In operation, the controller 104 or another component of the neuromodulation system 100 can control the optical source 222 to generate an optical signal (e.g., a polarized laser light pulse) that passes through the chamber and through the gaseous cesium. In some embodiments, the detection element can detect a polarization rotation of the optical signal after it passes through the chamber, which can be used to determine a cumulative component of the spin of the cesium atoms in the chamber. The controller 104 can receive the detected measurements of the optical signal (e.g., the polarization rotation) from the detection element and process them to measure the neural magnetic field and/or the corresponding neural electrical signals. For example, in some embodiments, the controller 104 can be configured to determine one or more of: a magnitude of the neural magnetic field, a distance from the optical magnetic sensor 220 to one or more of the target nerves, a magnitude of the neural electrical signals, and/or a temporal extent of the neural electrical signals.

While cesium has a high vapor pressure that permits high sensitivity measurements at the temperature of the human body, in other embodiments, other mediums can be used instead of cesium. Moreover, in other embodiments, the detection element can additionally or alternatively detect other properties of the optical signal that can be used to measure the neural magnetic field. Further, in some embodiments, the spin of the cesium atoms can be prepared (e.g., oriented in a known direction) by optical pumping or other suitable methods prior to transmitting the optical signal through the chamber.

Figure 3:
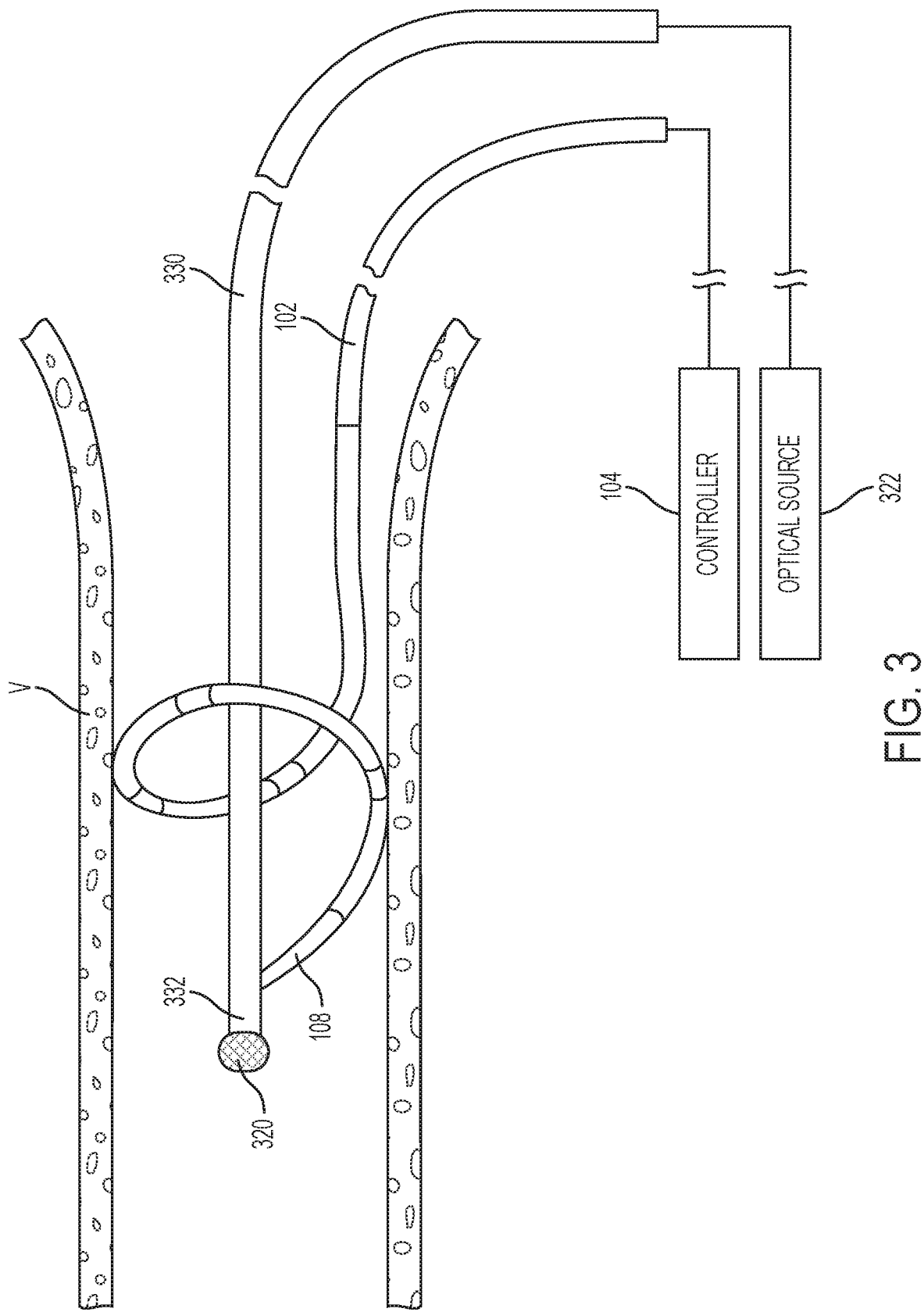
FIG. 3 is a partially schematic side view of the neuromodulation system shown in FIG. 1C with an optical magnetic sensor configured in accordance with embodiments of the present technology.

In some embodiments, the optical magnetic sensor can be a separate component from the neuromodulation catheter 102 that is also intravascularly positioned within the blood vessel V. For example, FIG. 3 is a partially schematic side view of the neuromodulation system 100 and including an optical magnetic sensor 320 in accordance with another embodiment of the present technology. The optical magnetic sensor 320 can have features generally similar to and operate generally similarly to the optical magnetic sensor 220 described above with reference to FIG. 2. However, in the illustrated embodiment, the optical magnetic sensor 320 is positioned on an optical catheter 330 that is separate from the neuromodulation catheter 102. As shown, the optical magnetic sensor 320 extends from a distal portion 332 of the optical catheter 330 and is positioned distally within the blood vessel V relative to the distal tip 108 of the neuromodulation catheter 102. In other embodiments, the optical magnetic sensor 320 can be disposed on or within a different portion of the optical catheter 330 (e.g., disposed within a proximal portion of the optical catheter 330) and/or can be positioned differently relative to the neuromodulation catheter 102 (e.g., positioned in the blood vessel V proximal to the distal tip 108). In some embodiments, the optical catheter 330 can be intravascularly positioned within the patient after the neuromodulation catheter 102 is positioned, as described in detail above with reference to FIGS. 1A-1C. In other embodiments, the optical catheter 330 can be positioned within the blood vessel V simultaneously with the neuromodulation catheter 102, or before the neuromodulation catheter 102. In certain embodiments, the optical catheter 330 can be advanced to the target site within the blood vessel V in a generally similar manner to the neuromodulation catheter 102 (e.g., advanced over a guidewire).

The optical magnetic sensor 320 can be optically coupled to an optical source (e.g., a laser light source) 322 via, for example, one or more optical fibers extending through a lumen of the optical catheter 330. The optical magnetic sensor 320 can further be operably coupled to the controller 104 and configured to communicate detected measurements of an optical signal generated by the optical source 322 to the controller 104. As described in detail above, the controller 104 can receive the detected measurements of the optical signal from the optical magnetic sensor 320 and process them to measure the neural magnetic field and/or the corresponding neural electrical signals. In some embodiments, the optical catheter 330 can be moved within the blood vessel V while the optical magnetic sensor 320 simultaneously detects the neural magnetic field to map (e.g., trace) a location or extent of the corresponding target nerves.

In certain embodiments, the optical magnetic sensor can be positioned externally to the human patient. For example, FIG. 4 illustrates gaining access to renal vasculature in accordance with some embodiments of the present technology. In the illustrated embodiment, the neuromodulation catheter 102 provides access to a renal plexus RP through an intravascular path P, such as a percutaneous access site in the femoral (illustrated), brachial, radial, or axillary artery to a targeted treatment site within a respective renal artery RA. By manipulating the proximal portion 106b of the elongated shaft 106 (FIGS. 1B and 1C) from outside the intravascular path P, an operator may advance the elongated shaft 106 through the sometimes tortuous intravascular path P and remotely manipulate the distal portion 106a of the elongated shaft 106 to the targeted treatment site. In the embodiment illustrated in FIG. 4A, the neuromodulation catheter 102 is delivered intravascularly to the treatment site using the guidewire 101 in an over-the-wire technique. As described in detail above, at the targeted treatment site, the guidewire 101 can be at least partially withdrawn or removed, and the neuromodulation catheter 102 can transform or otherwise be moved to the second (e.g., deployed) state (FIG. 1C).

Figure 4B:
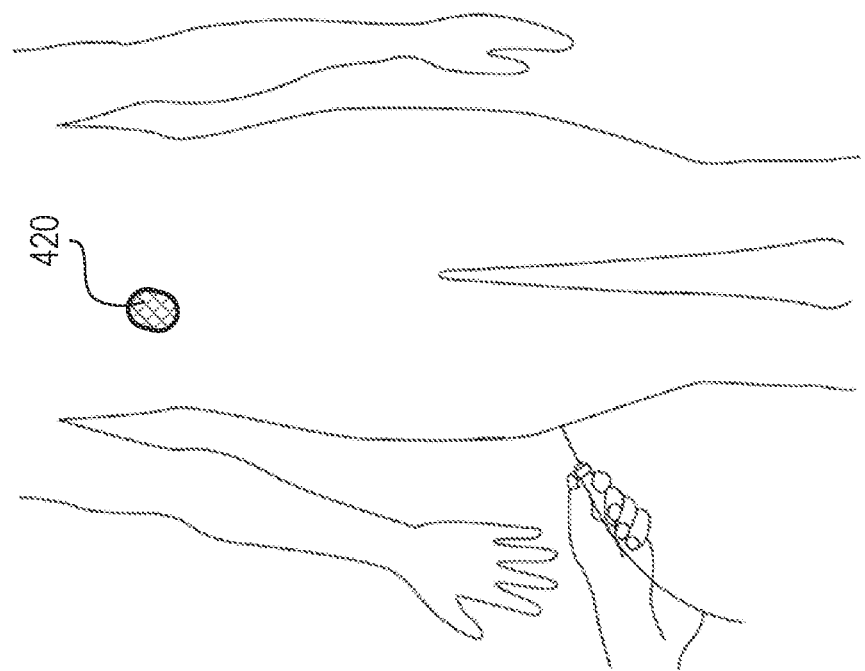
FIGS. 4A and 4B illustrate modulating renal nerves with the system of FIGS. 1A-1C and with an optical magnetic sensor configured in accordance with embodiments of the present technology.
Figure 4A:
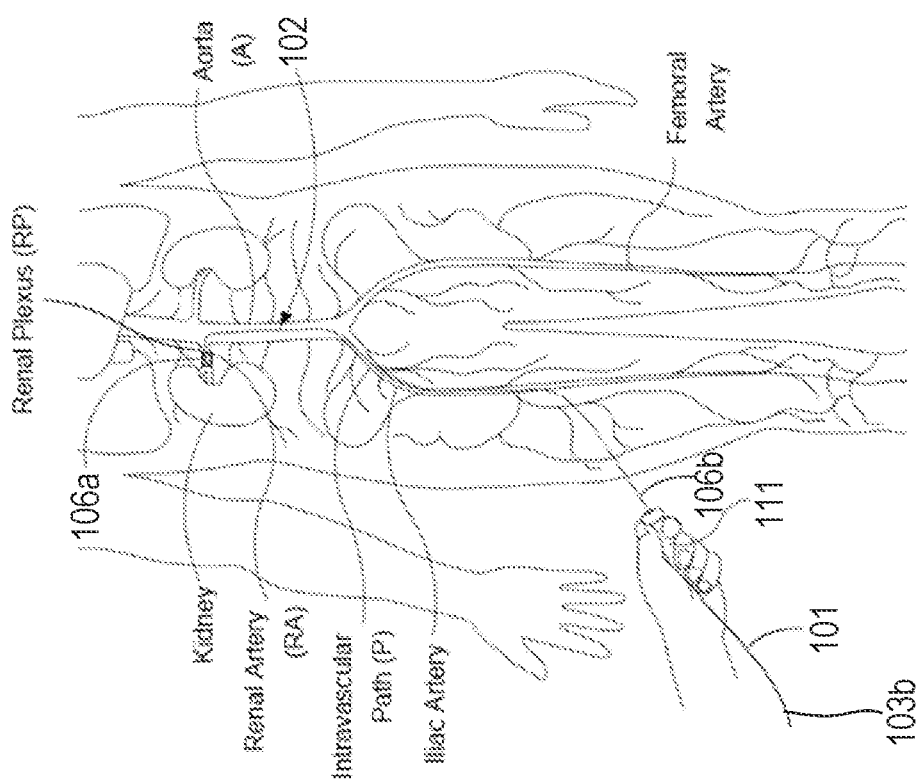

As shown in FIG. 4B, an optical magnetic sensor 420 can be positioned on or proximate to the patient's abdominal area while the distal portion of the neuromodulation catheter 102 is positioned within the patient's blood vessel V (e.g., the renal artery RA). That is, the optical magnetic sensor 420 can be positioned outside the patient and proximate to the patient's renal artery RA. The optical magnetic sensor 420 can have features generally similar to and operate generally similarly to the optical magnetic sensors 220 and 320 described above with reference to FIGS. 2 and 3, respectively. The optical magnetic sensor 420 can be coupled to an optical source (not pictured) and the controller 104 (FIGS. 1A-1C) and, as described in detail above, configured to detect properties of nerve impulses travelling along renal nerves proximate the renal artery RA. In other embodiments, the optical magnetic sensor 420 may be positioned elsewhere on the patient's body, such as the patient's arms, lower legs, and upper torso, or at the backside of the patient. For example, the optical magnetic sensor 420 can generally be positioned proximate to nerves targeted for the delivery of neuromodulation energy. Moreover, in certain embodiments, more than one optical magnetic sensor can be positioned externally to the patient. Likewise, in some embodiments, an intravascularly positioned optical magnetic sensor (FIGS. 2 and 3) can be used in addition to the externally positioned optical magnetic sensor 420.

In general, each of the embodiments described above with reference to FIGS. 2-4B advantageously enables the dynamic measurement of very small neural magnetic fields and the corresponding neural electrical impulses during a neuromodulation procedure. As described in detail below, such measurements may be made before and after the delivery of neuromodulation energy to, for example, determine the percentage that a target nerve or nerves are ablated by the neuromodulation energy during therapy. Furthermore, neural magnetic field measurements can be used to trace target nerves, to otherwise locate target nerves, to determine the location of ablations along target nerves, and/or to determine if target nerves have previously been ablated. By detecting and determining such information, the system 100 is expected to facilitate a more robust evaluation of a neuromodulation procedure as compared with many conventional neuromodulation systems. Moreover, in some embodiments, one or more parameters of neuromodulation therapy (e.g., a power, a time of energy delivery, etc.) or a position of the neuromodulation catheter 102 can be adjusted based on the measured neural magnetic field to, for example, particularize the neuromodulation therapy to the patient.

III. SELECTED EMBODIMENTS OF NEUROMODULATION SYSTEMS HAVING MAGNET ASSEMBLIES

In some embodiments, the neural magnetic field generated by the target nerves may be difficult to detect—for example, to distinguish from background noise—using an optical magnetic sensor alone. Accordingly, in certain embodiments, the neuromodulation system 100 can additionally include a magnet assembly configured to generate a variable magnetic field at or near the target nerves for amplifying the neural magnetic field and/or for enhancing the signal-to-noise ratio of the optical magnetic sensor.

Figure 5:
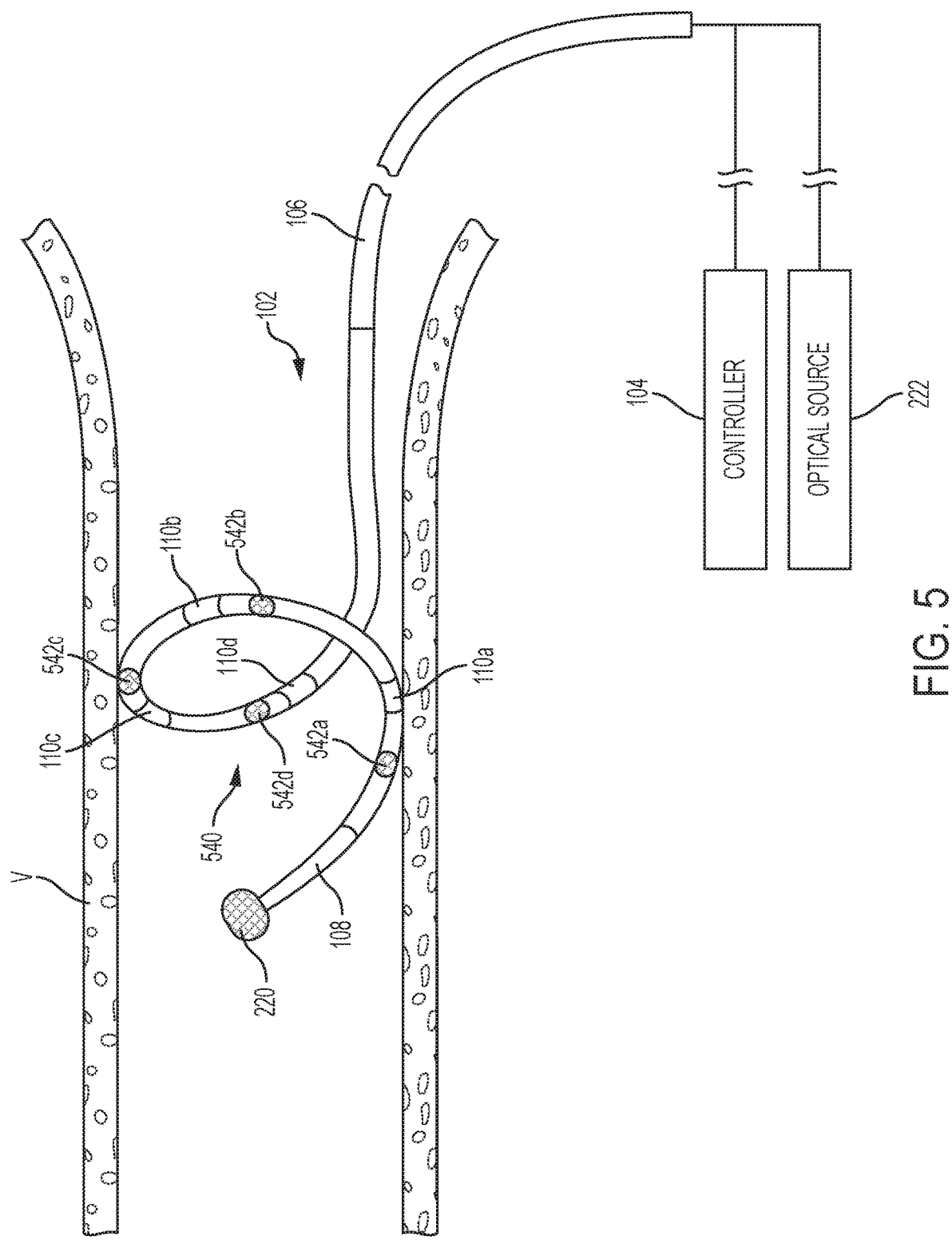
FIG. 5 is a partially schematic side view of the neuromodulation system shown in FIG. 2 with a magnet assembly configured in accordance with embodiments of the present technology.

In certain embodiments, the magnet assembly can include one or more electromagnets integrated with the neuromodulation catheter 102. FIG. 5, for example, is a partially schematic side view of the neuromodulation system 100 shown in FIG. 2 and including a magnet assembly 540 configured in accordance with embodiments of the present technology. As shown, the magnet assembly 540 includes a plurality of electromagnets 542 (identified individually as first through fourth electromagnets 542a-542d, respectively). In other embodiments, however, the magnet assembly 540 may include one, two, three, or more than four electromagnets 542. The electromagnets can be positioned within the neuromodulation catheter 102 or externally to the neuromodulation catheter 102 (e.g., similarly to the electrodes 110) and are configured to generate a variable magnetic field to amplify and/or enhance the neural magnetic field. For example, each electromagnet 542 can be electrically coupled to the controller 104 (e.g., via one or more wires extending through the neuromodulation catheter 102), and the controller 104 can be configured to generate a current through each of the electromagnets 542. A variable magnetic field can be produced by toggling (e.g., alternately powering and not powering) the electromagnets 542 and/or by varying the current through each electromagnet 542. In some embodiments, the controller 104 can control the electromagnets 542 to produce a variable magnetic field having a particular (e.g., known) shape, magnitude, profile, etc.

In the embodiment illustrated in FIG. 5, the electromagnets 542 are arranged proximate to corresponding ones of the electrodes 110. In other embodiments, the electromagnets 542 can have a different arrangement or a different number relative to the electrodes 110. Moreover, in certain embodiments, an optical catheter (FIG. 3) of the neuromodulation system 100 can additionally or alternatively include one or more electromagnets for generating the variable magnetic field.

Figure 6:
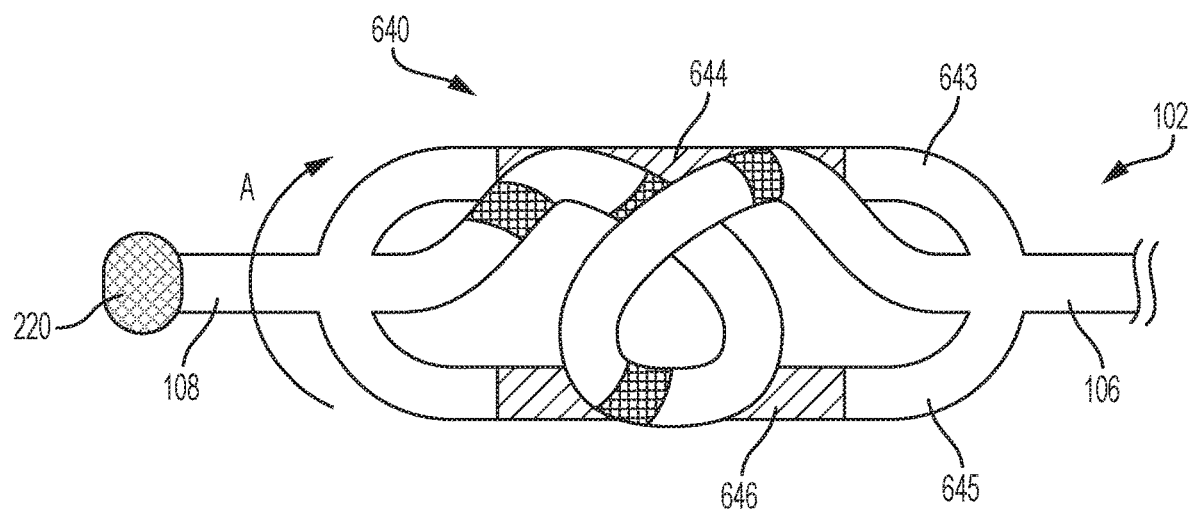
FIG. 6 is an enlarged side view of the neuromodulation system shown in FIG. 2 with a magnet assembly configured in accordance with embodiments of the present technology.

In some embodiments the neuromodulation system 100 can include one or more permanents magnets configured to move relative to the blood vessel V to generate a variable magnetic field at or near the target nerves. For example, FIG. 6 is an enlarged side view of the distal portion of the neuromodulation system 100 shown in FIG. 2 and including a magnet assembly 640 configured in accordance with embodiments of the present technology. As shown, the magnet assembly 640 includes a first arm 643 having a first permanent magnet 644 (e.g., a bar magnet) and a second arm 645 having a second permanent magnet 646. In the illustrated embodiment, the first and second arms 643, 645 extend from the elongated shaft 106 of the neuromodulation catheter 102 to the distal tip 108 of the neuromodulation catheter 102. In operation, the neuromodulation catheter 102 can be rotated (e.g., in the direction of the arrow A) within the blood vessel V. Movement of the first and second magnets 644, 646 creates a variable magnetic field that can enhance and/or amplify the neural magnetic field to enable more precise detection by the optical magnetic sensor 220. In some embodiments, a motor can be operably coupled to the neuromodulation catheter 102 and configured to rotate the magnet assembly 640. In other embodiments, an operator can manually rotate the neuromodulation catheter 102 to rotate the magnet assembly 640 and create a variable magnetic field. Although only two arms 643, 645 and two magnets 644, 646 are illustrated in the embodiment of FIG. 6, in other embodiments the magnet assembly 640 can include any number of arms and/or magnets (e.g., one arm having one magnet, three arms each having two magnets, etc.).

Figure 7:
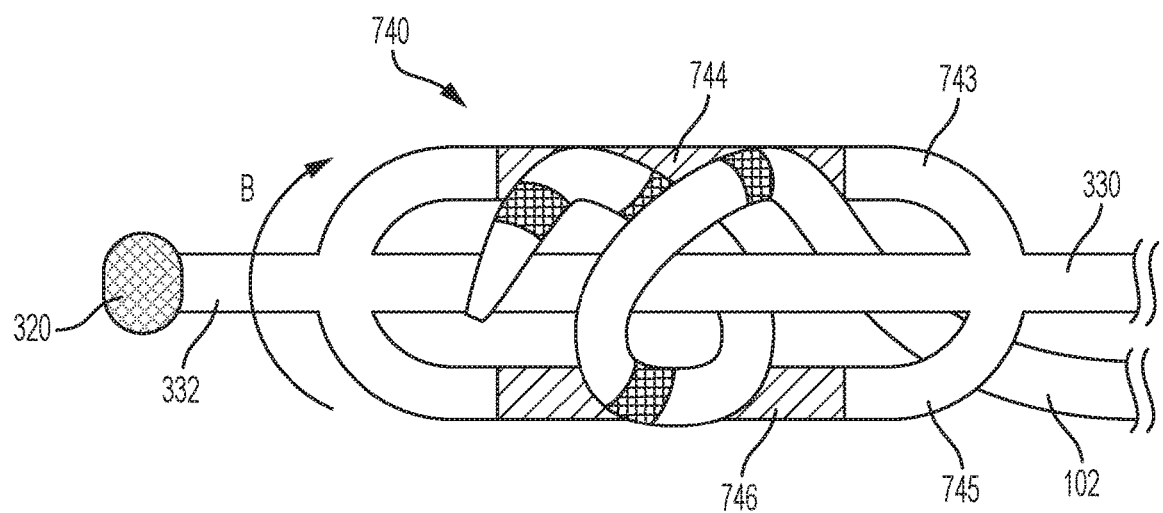
FIG. 7 is an enlarged side view of the neuromodulation system shown in FIG. 3 with a magnet assembly configured in accordance with embodiments of the present technology.

FIG. 7 is an enlarged side view of the distal portion of the neuromodulation system 100 shown in FIG. 3 and including a magnet assembly 740 configured in accordance with embodiments of the present technology. The magnet assembly 740 can have several features generally similar to the magnet assembly 640 described above with reference to FIG. 6. For example, the magnet assembly 740 includes a first arm 743 having a first permanent magnet 744 (e.g., a bar magnet) and a second arm 745 having a second permanent magnet 746. However, in the illustrated embodiment, the first and second arms 743, 745 extend from a proximal portion of the optical catheter 330 to the distal portion 332 of the optical catheter 330.

In operation, the optical catheter 330 can be rotated (e.g., in the direction of the arrow B) within the blood vessel V. Movement of the first and second magnets 744, 746 creates a variable magnetic field that can enhance and/or amplify the neural magnetic field to enable more precise detection by the optical magnetic sensor 320. In some embodiments, a motor can be operably coupled to the optical catheter 330 and configured to rotate the magnet assembly 740. In other embodiments, an operator can manually rotate the optical catheter 330 to rotate the magnet assembly 740 and create a variable magnetic field. In still other embodiments, the polarities of the first and second magnets 744, 746 may be changed rapidly in a pulsed fashion to create "virtual" rotation of the magnetic field. Although only two arms 743, 745 and two magnets 744, 746 are illustrated in the embodiment of FIG. 7, in other embodiments the magnet assembly 740 can include any number of arms and/or magnets (e.g., one arm having one magnet, three arms each having two magnets, etc.).

In some embodiments, the magnet assembly of the neuromodulation system 100 can have other configurations and comprise other components suitable for generating a variable magnetic field at the renal nerves. For example, in certain embodiments, the magnet assembly can comprise one or more permanent magnets that are configured to move relative to the blood vessel V and independently of the neuromodulation catheter 102 and/or the optical catheter 330. For example, in some embodiments, one or more magnets can be configured to move (e.g., translate, rotate, etc.) within the neuromodulation catheter 102 (e.g., within a lumen of the neuromodulation catheter 102) or within the optical catheter 330 without requiring movement of (e.g., rotation of) the neuromodulation catheter 102 or the optical catheter 330. In one particular embodiment, referring to FIGS. 6 and 7, the magnets 644, 646 and/or magnets 744, 746 can be configured to move proximally, move distally, and/or rotate within the arms 643, 645 and 743, 745, respectively, to generate the variable magnetic field.

In other embodiments, the magnet assembly can comprise a magnetic fluid that is introduced into the blood vessel V. For example, the magnetic fluid can be introduced proximate the target site in the blood vessel V via a lumen and a corresponding opening in the neuromodulation catheter 102. In still other embodiments, the magnet assembly need not be intravascularly positioned. For example, the patient can be placed within a MRI machine or other source capable of producing a variable magnetic field.

In some embodiments, the magnet assembly can include one or more electromagnets positioned on a balloon or a basket positioned at least partially at the distal portion of the neuromodulation catheter 102. In other embodiments, where the neuromodulation catheter 102 has a suitable configuration other than that illustrated in FIGS. 1A-1C, the magnet assembly can be adapted for the specific configuration. For example, in some embodiments, the neuromodulation catheter 102 can include a distal basket having ablation electrodes arranged on arms or other members of the basket. In such embodiments, electromagnets or permanent magnets can also be arranged on the arms or other members of the basket and configured to generate a variable magnetic field.

In any of the embodiments described above, the neuromodulation system 100 may include one or more components configured to magnetically shield the optical magnetic sensor from, for example, the variable magnetic field generated by the magnet assembly. In some embodiments, the variable magnetic field generated by the magnet assembly can have known properties (e.g., strength, vector direction, etc.) such that measurements of the neural magnetic field may be differentiated from the variable magnetic field generated by the magnet assembly.

IV. SELECTED EMBODIMENTS OF METHODS OF DETECTING AND MEASURING NEURAL ELECTRICAL SIGNALS FOR EVALUATING NEUROMODULATION THERAPY

Figure 8:
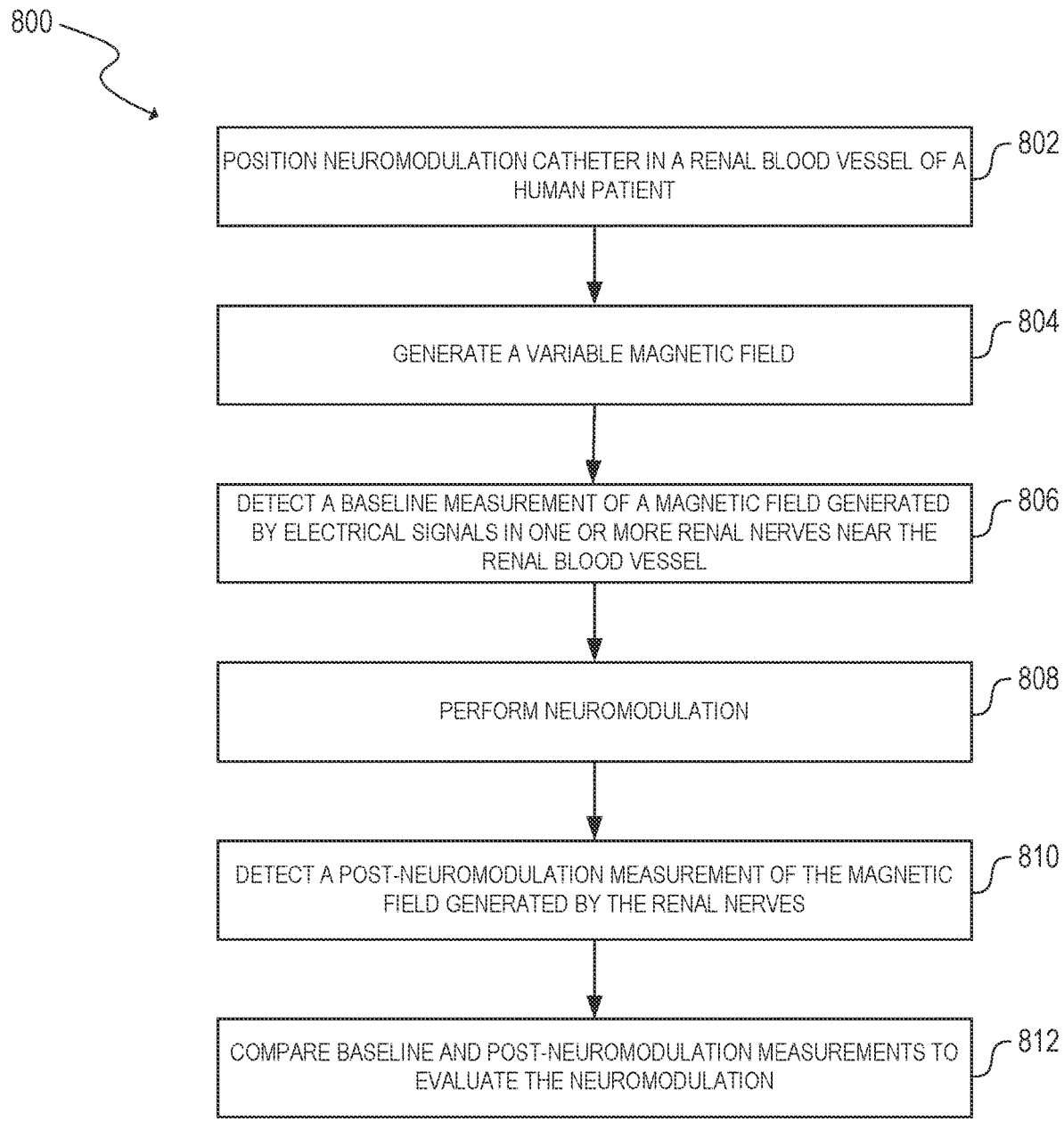
FIG. 8 is a flow diagram of a method or process of detecting and measuring neural electrical signals for evaluating neuromodulation therapy in accordance with embodiments of the present technology.

FIG. 8 is a flow diagram of a process or method 800 of detecting and measuring neural electrical signals for evaluating neuromodulation therapy in accordance with embodiments of the present technology. The method 800 can be implemented using the neuromodulation system 100 described above with reference to FIGS. 1A-7 and/or using other suitable systems. For example, the neuromodulation catheter 102, the optical magnetic sensor, the magnet assembly, and/or the controller 104 can be used to perform the various steps of the method 800. Accordingly, for sake of illustration, some features of the method 800 will be described in the context of the embodiments shown in FIGS. 1A-7.

Beginning at block 802, the method 800 includes positioning the neuromodulation catheter 102 at a target site within the blood vessel V of the human patient. In some embodiments, positioning the neuromodulation catheter 102 includes (i) positioning the guidewire 101 along a portion of the blood vessel V proximate the target site (FIG. 1A), (ii) advancing the neuromodulation catheter 102 over the guidewire 101 to the target site (FIG. 1B), and (iii) transforming or otherwise expanding the distal portion of the neuromodulation catheter 102 to the spiral/helical shape in which the electrodes 110 contact the wall of the blood vessel V (FIG. 1C).

At block 804, the method 800 can include generating a variable magnetic field using, for example, the magnet assembly of the neuromodulation system 100 to amplify and/or enhance the neural magnetic field generated by electrical impulses in renal nerves located proximate the wall of the blood vessel V. For example, in some embodiments, the magnet assembly can include one or more electromagnets and/or permanent magnets, and the controller 104 can generate a current through the electromagnets and/or cause the permanent magnets to move relative to the vessel V to generate a variable magnetic field at or near the renal nerves. In certain embodiments, the optical magnetic sensor can detect the neural magnetic field without amplification or enhancement. Accordingly, in some embodiments, the neuromodulation system 100 need not include a magnet assembly and/or the magnet assembly need to be used to generate a variable magnetic field. In such embodiments, the method can proceed directly from block 802 to block 806.

At block 806, the method 800 includes detecting a baseline measurement of the neural magnetic field using the optical magnetic sensor of the neuromodulation system 100. For example, as described in detail above, the baseline measurement can include one or more of: a magnitude of the neural magnetic field, a distance from the optical magnetic sensor to one or more of the renal nerves, a magnitude of the renal nerve impulses, and/or a temporal extent of the renal nerve impulses. More particularly, in some embodiments, the controller 104 can cause an optical source to generate a laser pulse that passes through a chamber of the optical magnetic sensor including gaseous cesium. A detection element of the optical sensor can measure a component of the laser light (e.g., a polarization rotation) after it passes through the chamber and communicate the measurement to the controller 104, and the controller 104 can then process the measurement to determine the baseline measurement of the neural magnetic field. The baseline measurement can be a single measurement or a composite or average of several different measurements. In certain embodiments, the baseline measurement can be used to determine a property of the renal nerves such as, for example, a location or extent of targeted renal nerves and/or a location of ablation (e.g., from a previous neuromodulation procedure) at one or more of targeted renal nerves. In some embodiments, the obtained measurements can be communicated to and stored in the memory of the controller 104 and/or another component of the neuromodulation system 100.

At block 808, the method 800 includes performing neuromodulation therapy with the neuromodulation catheter 102 at the target site in the blood vessel V to, for example, ablate the renal nerves proximate to the wall of the blood vessel V. For example, the method 800 can include applying RF energy (e.g., via the electrodes 110), pulsed electrical energy, microwave energy, optical energy, ultrasound energy (e.g., intravascularly delivered ultrasound and/or HIFU), direct heat energy, radiation, cryogenic cooling, chemical-based treatment, and/or another suitable type of neuromodulation energy.

At block 810, the method 800 includes detecting a post-neuromodulation measurement of the neural magnetic field using the optical magnetic sensor of the neuromodulation system 100. In some embodiments, a variable magnetic field can be generated before and/or during detection of the post-neuromodulation measurement as described above with reference to block 804. The optical magnetic sensor of the neuromodulation system 100 can be used to detect the post-neuromodulation measurement in generally the same manner as described above with reference to block 806. The post-modulation measurement can include a single measurement or a composite or average of several different measurements. In some embodiments, the detected post-neuromodulation measurements are communicated to the controller 104 and stored in the memory of the controller 104 and/or another component of the neuromodulation system 100.

At block 812, the method includes comparing the detected baseline measurement (block 806) and the detected post-neuromodulation measurement (block 810) to, for example, evaluate the neuromodulation performed at the target site (block 808). For example, in some embodiments, the comparison can be used to determine a percentage that targeted renal nerves were ablated as a result of the neuromodulation energy delivered by the neuromodulation catheter 102. Specifically, a reduction in the magnitude (or another property) of the neural magnetic field after neuromodulation can indicate a reduction in renal neural activity and, therefore, that ablation was at least partially successful. In certain embodiments, the comparison can alternatively or additionally be used to determine a specific location of an ablation along a targeted renal nerve. In some embodiments, the comparison can be performed automatically by the controller 104 and/or another component of the neuromodulation system 100. In other embodiments, the post-neuromodulation measurement alone can be used to determine a location of ablation along the targeted renal nerve.

In some embodiments, the method 800 can further include repositioning the neuromodulation catheter 102 and/or adjusting one or more parameters of neuromodulation therapy based on the baseline measurement, the post-neuromodulation measurement, and/or the comparison of the two. For example, in certain embodiments, the amount of power and/or the length of power delivery of subsequent neuromodulation can be adjusted based on a previously determined percentage of renal nerve ablation. In some embodiments, if substantially no renal neural activity is detected post-neuromodulation, the operator or the system 100 can determine that no further neuromodulation is necessary. Similarly, the position of the neuromodulation catheter 102 can be adjusted based on a previously determined location of ablations along a renal nerve. In certain embodiments, the comparison, the percentage of renal nerve ablation, the location of an ablation, etc., can be displayed to an operator of the neuromodulation system 100 (e.g., on the console in real-time or near-real time) to permit further adjustments to a neuromodulation procedure.

Accordingly, by measuring a neural magnetic field both before and after neuromodulation energy is delivered to a patient, the method 800 can advantageously (i) provide useful information for evaluating a neuromodulation procedure and (ii) enable the customization of a neuromodulation procedure for a particular patient. As such, embodiments of the present technology are expected to increase the efficacy of neuromodulation procedures.

V. SELECTED EXAMPLES OF NEUROMODULATION DEVICES AND RELATED SYSTEMS

Figure 9:
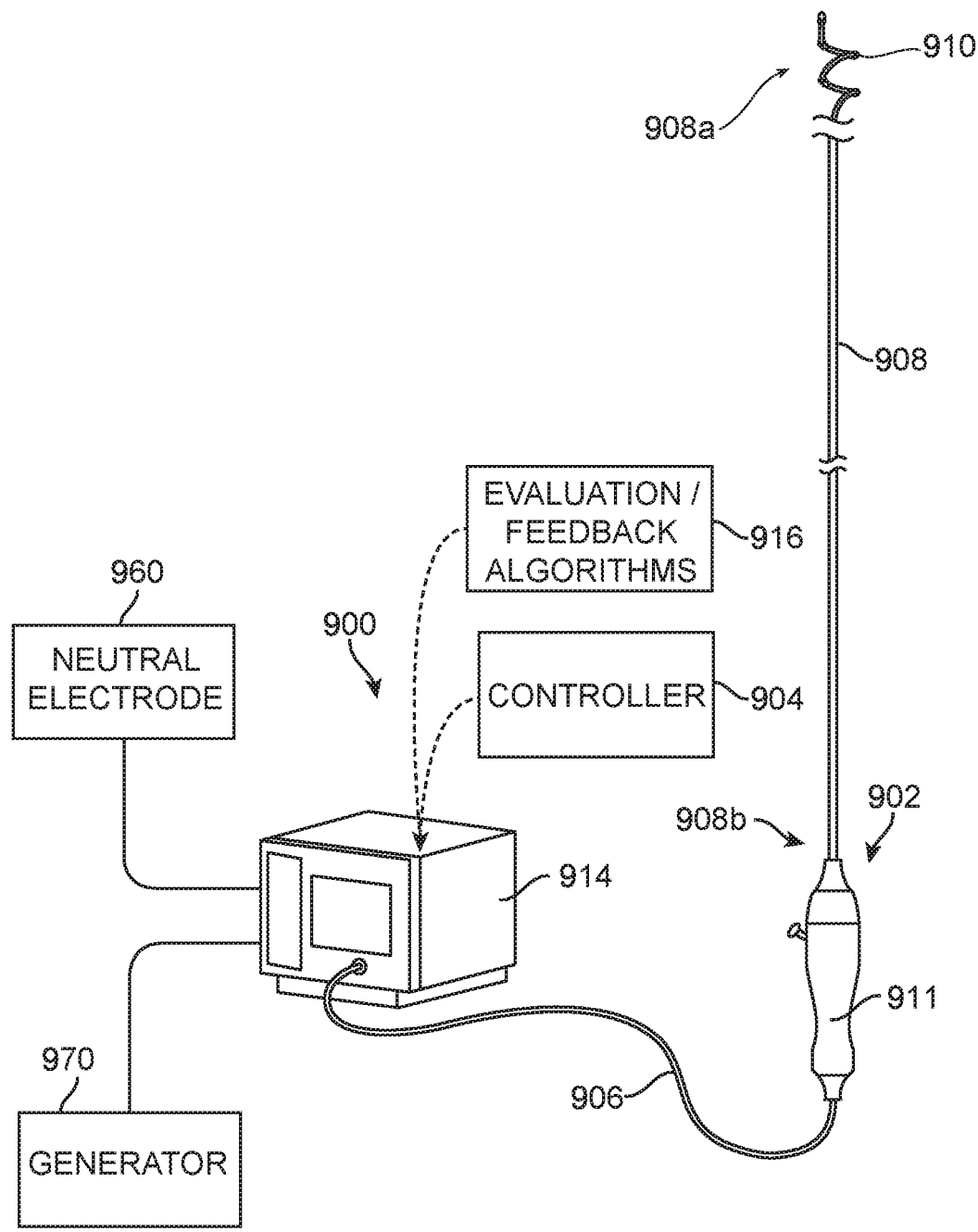
FIG. 9 is a partially schematic illustration of a neuromodulation system configured in accordance with another embodiment of the present technology.

FIG. 9 is a partially schematic illustration of a therapeutic system 900 ("system 900") configured in accordance with an embodiment of the present technology. The system 900 can include various features similar to the neuromodulation system 100 described above with reference to FIGS. 1A-7. In addition, the system 900 can be used to implement any of the methods described herein. As shown in FIG. 9, the system 900 includes a neuromodulation catheter 902, a console 914, and a cable 906 extending therebetween. The neuromodulation catheter 902 can include an elongated shaft 908 having a proximal portion 908b, a distal portion 908a, and a handle 911 operably connected to the elongated shaft 908 at the proximal portion 908b. The elongated shaft 908 can be 2, 3, 4, 5, 6, or 7 French or another suitable size. As shown in FIG. 9, one or more electrodes 910 can be spaced along the distal portion 908a of the elongated shaft 908. The electrodes 910 can be configured to apply electrical stimuli (e.g., radio frequency (RF) energy) to target sites at or proximate to vessels within a patient, temporarily stun nerves, deliver neuromodulation energy to target sites, and/or detect vessel impedance. In various embodiments, certain electrodes 910 can be dedicated to applying stimuli and/or detecting impedance, and the neuromodulation catheter 902 can include other types of therapeutic elements that provide neuromodulation therapy using various modalities, such cryotherapeutic cooling, ultrasound energy, etc. In some embodiments, the neuromodulation catheter 902 can further include (i) an optical magnetic sensor, such as one of such sensors described herein, configured to detect magnetic field(s) generated by nerves proximate the wall of a blood vessel before/after energy delivery and/or (ii) a magnet assembly for amplifying and/or enhancing the magnetic field(s).

The console 914 can be configured to control, monitor, supply, and/or otherwise support operation of the neuromodulation catheter 902. In addition, the console 914 can be configured to provide feedback to an operator before, during, and/or after a treatment procedure via an evaluation/feedback algorithm 916. The console 914 can further be configured to generate a selected form and/or magnitude of energy for delivery to tissue at the treatment site via the electrodes 910, and therefore the console 914 may have different configurations depending on the treatment modality of the neuromodulation catheter 902. For example, when the neuromodulation catheter 902 is configured for electrode-based, heat-element-based, or transducer-based treatment, the console 914 can include an energy generator 970 (shown schematically) configured to generate RP energy (e.g., monopolar and/or bipolar RF energy), pulsed energy, microwave energy, optical energy, ultrasound energy (e.g., intravascularly delivered ultrasound and/or high-intensity focused ultrasound (HIFU)), direct heat energy, radiation (e.g., infrared, visible, and/or gamma radiation), and/or another suitable type of energy. In this configuration, the console 914 can also include evaluation/feedback algorithms 916 for controlling the electrodes 910. In selected embodiments, the energy generator 970 can be configured to deliver a monopolar electric field via one or more of the electrodes 910. In such embodiments, a neutral or dispersive electrode 960 may be electrically coupled to the energy generator 970 and attached to the exterior of the patient. When the neuromodulation catheter 902 is configured for cryotherapeutic treatment, the console 914 can include a refrigerant reservoir (not shown), and can be configured to supply the neuromodulation catheter 902 with refrigerant. Similarly, when the neuromodulation catheter 902 is configured for chemical-based treatment (e.g., drug infusion), the console 914 can include a chemical reservoir (not shown) and can be configured to supply the neuromodulation catheter 902 with one or more chemicals.

In various embodiments, the system 900 can further include a controller 904 communicatively coupled to the neuromodulation catheter 902. The controller 904 can be configured to initiate, terminate, and/or adjust operation of one or more components (e.g., the electrodes 910) of the neuromodulation catheter 902 directly and/or via the console 914 and/or via a wired or wireless communication link. In various embodiments, the system 900 can include multiple controllers. In other embodiments, the neuromodulation catheter 902 can be communicatively coupled to a single controller 904. The controller(s) 904 can be integrated with the console 914 or the handle 911 positioned outside the patient and used to operate the system 900. In other embodiments, the controller 904 can be omitted or have other suitable locations (e.g., within the handle 911, along the cable 906, etc.). The controller 904 can include computer-implemented instructions to initiate, terminate, and/or adjust operation of one or more components of the neuromodulation catheter 902 directly and/or via another aspect of the system (e.g., the console 914 and/or handle 911). For example, the controller 904 can further provide instructions to the neuromodulation catheter 902 to apply neuromodulatory energy to the treatment site (e.g., RF energy via the electrodes 910). The controller 904 can be configured to execute an automated control algorithm and/or to receive control instructions from an operator. Further, the controller 904 can include or be linked to the evaluation/feedback algorithm 916 that can provide feedback to an operator before, during, and/or after a treatment procedure via a console, monitor, and/or other user interface.

The distal end of the neuromodulation catheter 902 may define a passageway for receiving a guidewire (not shown) for delivery of the neuromodulation catheter 902 using either OTW or RX techniques. At the treatment site, the guidewire can be at least partially withdrawn or removed, and the distal portion of the neuromodulation catheter 902 can transform or otherwise be moved to a deployed arrangement for recording neural activity and/or delivering energy at the treatment site. In other embodiments, the neuromodulation catheter 902 may be delivered to the treatment site within a guide sheath (not shown) with or without using the guidewire. When the neuromodulation catheter 902 is at the target site, the guide sheath may be at least partially withdrawn or retracted and the distal portion of the neuromodulation catheter 902 can be transformed into the deployed arrangement. In still other embodiments, the elongated shaft 908 may be steerable itself such that the neuromodulation catheter 902 may be delivered to the treatment site without the aid of the guidewire and/or guide sheath.

Image guidance, e.g., computed tomography (CT), fluoroscopy, intravascular ultrasound (IVUS), optical coherence tomography (OCT), intracardiac echocardiography (ICE), or another suitable image guidance modality, or combinations thereof, may be used to aid the clinician's positioning and manipulation of the neuromodulation catheter 902. For example, a fluoroscopy system (e.g., including a flat-panel detector, x-ray, or c-arm) can be rotated to accurately visualize and identify the target treatment site. In other embodiments, the treatment site can be determined using IVUS, OCT, and/or other suitable image mapping modalities that can correlate the target treatment site with an identifiable anatomical structure (e.g., a spinal feature) and/or a radiopaque ruler (e.g., positioned under or on the patient) before delivering the neuromodulation catheter 902. Further, in some embodiments, image guidance components (e.g., IVUS, OCT) may be integrated with the neuromodulation catheter 902 and/or run in parallel with the neuromodulation catheter 902 to provide image guidance during positioning of the neuromodulation catheter 902. For example, image guidance components (e.g., IVUS or OCT) can be coupled to the neuromodulation catheter 902 to provide three-dimensional images of the vasculature proximate the target site to facilitate positioning or deploying the multi-electrode assembly within the target renal blood vessel.

Energy from the electrodes 910 (FIG. 9) and/or other energy delivery elements may then be applied to target tissue to induce one or more desired neuromodulating effects on localized regions of the renal artery RA and adjacent regions of the renal plexus RP, which lay intimately within, adjacent to, or in close proximity to the adventitia of the renal artery RA. The purposeful application of the energy may achieve neuromodulation along all or at least a portion of the renal plexus RP. The neuromodulating effects are generally a function of, at least in part, power, time, contact between the energy delivery elements and the vessel wall, and blood flow through the vessel. The neuromodulating effects may include denervation, thermal ablation, and/or non-ablative thermal alteration or damage (e.g., via sustained heating and/or resistive heating). Desired thermal heating effects may include raising the temperature of target neural fibers above a desired threshold to achieve non-ablative thermal alteration, or above a higher temperature to achieve ablative thermal alteration. For example, the target temperature may be above body temperature (e.g., approximately 37° C.) but less than about 45° C. for non-ablative thermal alteration, or the target temperature may be about 45° C. or higher for the ablative thermal alteration. Desired non-thermal neuromodulation effects may include altering the electrical signals transmitted in a nerve.

VI. RENAL NEUROMODULATION

Renal neuromodulation is the partial or complete incapacitation or other effective disruption of nerves of the kidneys (e.g., nerves terminating in the kidneys or in structures closely associated with the kidneys). In particular, renal neuromodulation can include inhibiting, reducing, and/or blocking neural communication along neural fibers (e.g., efferent and/or afferent neural fibers) of the kidneys. Such incapacitation can be long-term (e.g., permanent or for periods of months, years, or decades) or short-term (e.g., for periods of minutes, hours, days, or weeks). Renal neuromodulation is expected to contribute to the systemic reduction of sympathetic tone or drive and/or to benefit at least some specific organs and/or other bodily structures innervated by sympathetic nerves. Accordingly, renal neuromodulation is expected to be useful in treating clinical conditions associated with systemic sympathetic over activity or hyperactivity, particularly conditions associated with central sympathetic overstimulation. For example, renal neuromodulation is expected to efficaciously treat hypertension, heart failure, acute myocardial infarction, metabolic syndrome, insulin resistance, diabetes, left ventricular hypertrophy, chronic and end stage renal disease, inappropriate fluid retention in heart failure, cardio renal syndrome, polycystic kidney disease, polycystic ovary syndrome, osteoporosis, erectile dysfunction, and sudden death, among other conditions.

Renal neuromodulation can be electrically-induced, thermally-induced, chemically-induced, or induced in another suitable manner or combination of manners at one or more suitable treatment sites during a treatment procedure. The treatment site can be within or otherwise proximate to a renal lumen (e.g., a renal artery, a ureter, a renal pelvis, a major renal calyx, a minor renal calyx, or another suitable structure), and the treated tissue can include tissue at least proximate to a wall of the renal lumen. For example, with regard to a renal artery, a treatment procedure can include modulating nerves in the renal plexus, which lay intimately within or adjacent to the adventitia of the renal artery.

Renal neuromodulation can include a cryotherapeutic treatment modality alone or in combination with another treatment modality. Cryotherapeutic treatment can include cooling tissue at a treatment site in a manner that modulates neural function. For example, sufficiently cooling at least a portion of a sympathetic renal nerve can slow or potentially block conduction of neural signals to produce a prolonged or permanent reduction in renal sympathetic activity. This effect can occur as a result of cryotherapeutic tissue damage, which can include, for example, direct cell injury (e.g., necrosis), vascular or luminal injury (e.g., starving cells from nutrients by damaging supplying blood vessels), and/or sublethal hypothermia with subsequent apoptosis. Exposure to cryotherapeutic cooling can cause acute cell death (e.g., immediately after exposure) and/or delayed cell death (e.g., during tissue thawing and subsequent hyperperfusion). Neuromodulation using a cryotherapeutic treatment in accordance with embodiments of the present technology can include cooling a structure proximate an inner surface of a body lumen wall such that tissue is effectively cooled to a depth where sympathetic renal nerves reside. For example, in some embodiments, a cooling assembly of a cryotherapeutic device can be cooled to the extent that it causes therapeutically-effective, cryogenic renal neuromodulation. In other embodiments, a cryotherapeutic treatment modality can include cooling that is not configured to cause neuromodulation. For example, the cooling can be at or above cryogenic temperatures and can be used to control neuromodulation via another treatment modality (e.g., to protect tissue from neuromodulating energy).

Renal neuromodulation can include an electrode-based or transducer-based treatment modality alone or in combination with another treatment modality. Electrode-based or transducer-based treatment can include delivering electricity and/or another form of energy to tissue at a treatment location to stimulate and/or heat the tissue in a manner that modulates neural function. For example, sufficiently stimulating and/or heating at least a portion of a sympathetic renal nerve can slow or potentially block conduction of neural signals to produce a prolonged or permanent reduction in renal sympathetic activity. A variety of suitable types of energy can be used to stimulate and/or heat tissue at a treatment location. For example, neuromodulation in accordance with embodiments of the present technology can include delivering RF energy, pulsed energy, microwave energy, optical energy, focused ultrasound energy (e.g., HIFU energy), or another suitable type of energy alone or in combination. An electrode or transducer used to deliver this energy can be used alone or with other electrodes or transducers in a multi-electrode or multi-transducer array. Furthermore, the energy can be applied from within the body (e.g., within the vasculature or other body lumens in a catheter-based approach) and/or from outside the body (e.g., via an applicator positioned outside the body). Furthermore, energy can be used to reduce damage to non-targeted tissue when targeted tissue adjacent to the non-targeted tissue is subjected to neuromodulating cooling.

Neuromodulation using focused ultrasound energy (e.g., HIFU energy) can be beneficial relative to neuromodulation using other treatment modalities. Focused ultrasound is an example of a transducer-based treatment modality that can be delivered from outside the body. Focused ultrasound treatment can be performed in close association with imaging (e.g., magnetic resonance, computed tomography, fluoroscopy, optical coherence tomography, or another suitable imaging modality). For example, imaging can be used to identify an anatomical position of a treatment location (e.g., as a set of coordinates relative to a reference point). The coordinates can then entered into a focused ultrasound device configured to change the power, angle, phase, or other suitable parameters to generate an ultrasound focal zone at the location corresponding to the coordinates. The focal zone can be small enough to localize therapeutically-effective heating at the treatment location while partially or fully avoiding potentially harmful disruption of nearby structures. To generate the focal zone, the ultrasound device can be configured to pass ultrasound energy through a lens, and/or the ultrasound energy can be generated by a curved transducer or by multiple transducers in a phased array (curved or straight).

Heating effects of electrode-based or transducer-based treatment can include ablation and/or non-ablative alteration or damage (e.g., via sustained heating and/or resistive heating). For example, a treatment procedure can include raising the temperature of target neural fibers to a target temperature above a first threshold to achieve non-ablative alteration, or above a second, higher threshold to achieve ablation. The target temperature can be higher than about body temperature (e.g., about 37° C.) but less than about 45° C. for non-ablative alteration, and the target temperature can be higher than about 45° C. for ablation. Heating tissue to a temperature between about body temperature and about 45° C. can induce non-ablative alteration, for example, via moderate heating of target neural fibers or of vascular or luminal structures that perfuse the target neural fibers. In cases where vascular structures are affected, the target neural fibers can be denied perfusion resulting in necrosis of the neural tissue. Heating tissue to a target temperature higher than about 45° C. (e.g., higher than about 60° C.) can induce ablation, for example, via substantial heating of target neural fibers or of vascular or luminal structures that perfuse the target fibers. In some patients, it can be desirable to heat tissue to temperatures that are sufficient to ablate the target neural fibers or the vascular or luminal structures, but that are less than about 90° C. (e.g., less than about 85° C., less than about 80° C., or less than about 75° C.).

Renal neuromodulation can include a chemical-based treatment modality alone or in combination with another treatment modality. Neuromodulation using chemical-based treatment can include delivering one or more chemicals (e.g., drugs or other agents) to tissue at a treatment location in a manner that modulates neural function. The chemical, for example, can be selected to affect the treatment location generally or to selectively affect some structures at the treatment location over other structures. The chemical, for example, can be guanethidine, ethanol, phenol, a neurotoxin, or another suitable agent selected to alter, damage, or disrupt nerves. A variety of suitable techniques can be used to deliver chemicals to tissue at a treatment location. For example, chemicals can be delivered via one or more needles originating outside the body or within the vasculature or other body lumens. In an intravascular example, a catheter can be used to intravascularly position a therapeutic element including a plurality of needles (e.g., microneedles) that can be retracted or otherwise blocked prior to deployment. In other embodiments, a chemical can be introduced into tissue at a treatment location via simple diffusion through a body lumen wall, electrophoresis, or another suitable mechanism. Similar techniques can be used to introduce chemicals that are not configured to cause neuromodulation, but rather to facilitate neuromodulation via another treatment modality.

VII. RELATED ANATOMY AND PHYSIOLOGY

As noted previously, the sympathetic nervous system (SNS) is a branch of the autonomic nervous system along with the enteric nervous system and parasympathetic nervous system. It is always active at a basal level (called sympathetic tone) and becomes more active during times of stress. Like other parts of the nervous system, the sympathetic nervous system operates through a series of interconnected neurons. Sympathetic neurons are frequently considered part of the peripheral nervous system (PNS), although many lie within the central nervous system (CNS). Sympathetic neurons of the spinal cord (which is part of the CNS) communicate with peripheral sympathetic neurons via a series of sympathetic ganglia. Within the ganglia, spinal cord sympathetic neurons join peripheral sympathetic neurons through synapses. Spinal cord sympathetic neurons are therefore called presynaptic (or preganglionic) neurons, while peripheral sympathetic neurons are called postsynaptic (or postganglionic) neurons.

At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release noradrenaline (norepinephrine). Prolonged activation may elicit the release of adrenaline from the adrenal medulla.

Once released, norepinephrine and epinephrine bind adrenergic receptors on peripheral tissues. Binding to adrenergic receptors causes a neuronal and hormonal response. The physiologic manifestations include pupil dilation, increased heart rale, occasional vomiting, and increased blood pressure. Increased sweating is also seen due to binding of cholinergic receptors of the sweat glands.

The sympathetic nervous system is responsible for up- and down-regulating many homeostatic mechanisms in living organisms. Fibers from the SNS innervate tissues in almost every organ system, providing at least some regulatory function to physiological features as diverse as pupil diameter, gut motility, and urinary output. This response is also known as sympatho-adrenal response of the body, as the preganglionic sympathetic fibers that end in the adrenal medulla (but also all other sympathetic fibers) secrete acetylcholine, which activates the secretion of adrenaline (epinephrine) and to a lesser extent noradrenaline (norepinephrine). Therefore, this response that acts primarily on the cardiovascular system is mediated directly via impulses transmitted through the sympathetic nervous system and indirectly via catecholamines secreted from the adrenal medulla.

Science typically looks at the SNS as an automatic regulation system, that is, one that operates without the intervention of conscious thought. Some evolutionary theorists suggest that the sympathetic nervous system operated in early organisms to maintain survival as the sympathetic nervous system is responsible for priming the body for action. One example of this priming is in the moments before waking, in which sympathetic outflow spontaneously increases in preparation for action.

A. The Sympathetic Chain

Figure 10:
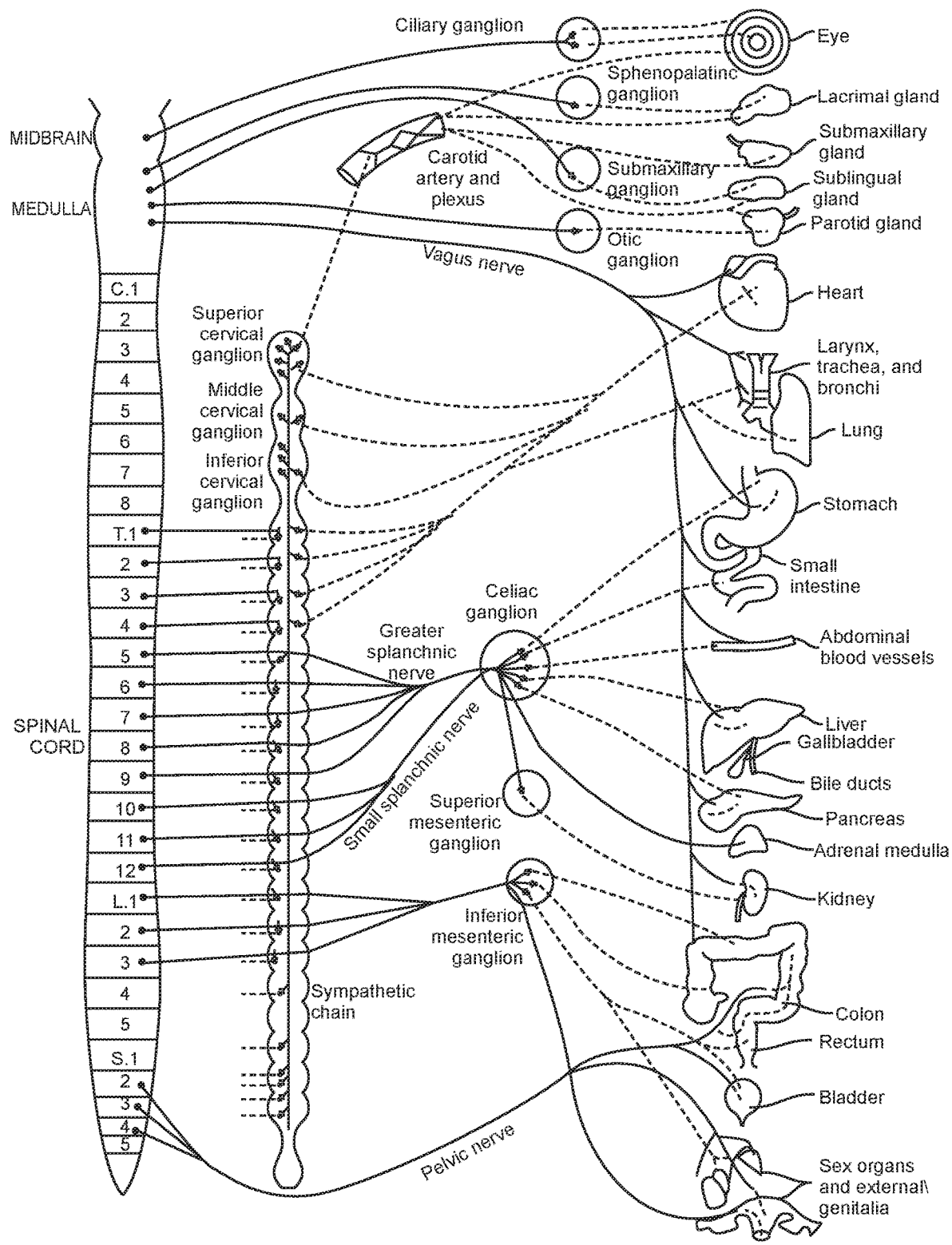
FIG. 10 is a conceptual illustration of the sympathetic nervous system (SNS) and how the brain communicates with the body via the SNS.

As shown in FIG. 10, the SNS provides a network of nerves that allows the brain to communicate with the body. Sympathetic nerves originate inside the vertebral column, toward the middle of the spinal cord in the intermediolateral cell column (or lateral horn), beginning at the first thoracic segment of the spinal cord and are thought to extend to the second or third lumbar segments. Because its cells begin in the thoracic and lumbar regions of the spinal cord, the SNS is said to have a thoracolumbar outflow. Axons of these nerves leave the spinal cord through the anterior rootlet/root. They pass near the spinal (sensory) ganglion, where they enter the anterior rami of the spinal nerves. However, unlike somatic innervation, they quickly separate out through white rami connectors which connect to either the paravertebral (which lie near the vertebral column) or prevertebral (which lie near the aortic bifurcation) ganglia extending alongside the spinal column.

In order to reach the target organs and glands, the axons should travel long distances in the body, and, to accomplish this, many axons relay their message to a second cell through synaptic transmission. The ends of the axons link across a space, the synapse, to the dendrites of the second cell. The first cell (the presynaptic cell) sends a neurotransmitter across the synaptic cleft where it activates the second cell (the postsynaptic cell). The message is then carried to the final destination.

In the SNS and other components of the peripheral nervous system, these synapses are made at sites called ganglia, discussed above. The cell that sends its fiber is called a preganglionic cell, while the cell whose fiber leaves the ganglion is called a postganglionic cell. As mentioned previously, the preganglionic cells of the SNS are located between the first thoracic (T1) segment and third lumbar (L3) segments of the spinal cord. Postganglionic cells have their cell bodies in the ganglia and send their axons to target organs or glands.

The ganglia include not just the sympathetic trunks but also the cervical ganglia (superior, middle and inferior), which sends sympathetic nerve fibers to the head and thorax organs, and the celiac and mesenteric ganglia (which send sympathetic fibers to the gut).

1. Innervation of the Kidneys

Figure 11:
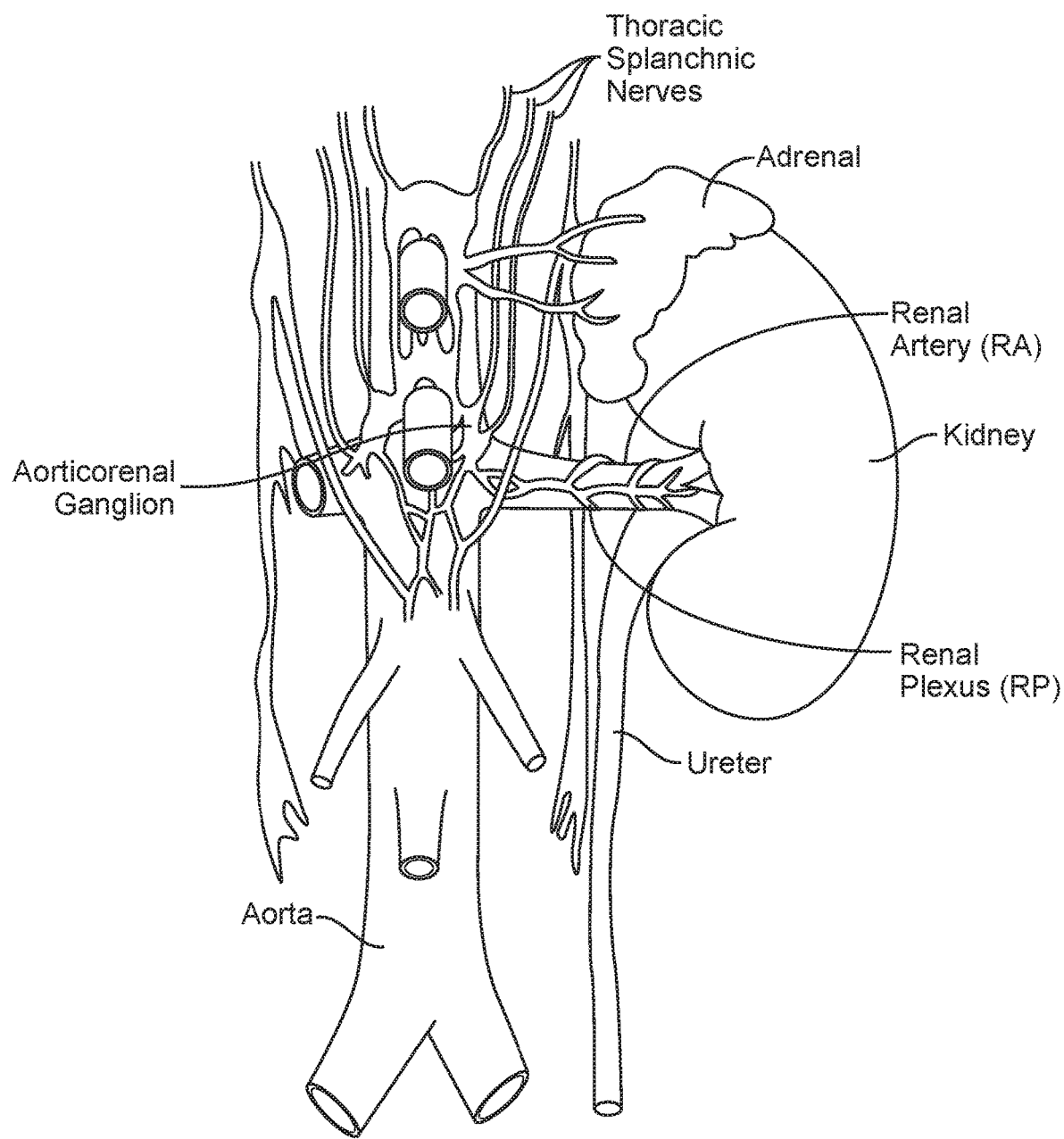
FIG. 11 is an enlarged anatomic view of nerves innervating a left kidney to form the renal plexus surrounding the left renal artery.

As FIG. 11 shows, the kidney is innervated by the renal plexus (RP), which is intimately associated with the renal artery. The renal plexus (RP) is an autonomic plexus that surrounds the renal artery and is embedded within the adventitia of the renal artery. The renal plexus (RP) extends along the renal artery until it arrives at the substance of the kidney. Fibers contributing to the renal plexus (RP) arise from the celiac ganglion, the superior mesenteric ganglion, the aorticorenal ganglion and the aortic plexus. The renal plexus (RP), also referred to as the renal nerve, is predominantly comprised of sympathetic components. There is no (or at least very minimal) parasympathetic innervation of the kidney.

Preganglionic neuronal cell bodies are located in the intermediolateral cell column of the spinal cord. Preganglionic axons pass through the paravertebral ganglia (they do not synapse) to become the lesser splanchnic nerve, the least splanchnic nerve, first lumbar splanchnic nerve, second lumbar splanchnic nerve, and travel to the celiac ganglion, the superior mesenteric ganglion, and the aorticorenal ganglion. Postganglionic neuronal cell bodies exit the celiac ganglion, the superior mesenteric ganglion, and the aorticorenal ganglion to the renal plexus (RP) and are distributed to the renal vasculature.

2. Renal Sympathetic Neural Activity

Messages travel through the SNS in a bidirectional flow. Efferent messages may trigger changes in different parts of the body simultaneously. For example, the sympathetic nervous system may accelerate heart rate; widen bronchial passages; decrease motility (movement) of the large intestine; constrict blood vessels; increase peristalsis in the esophagus; cause pupil dilation, piloerection (goose bumps) and perspiration (sweating); and raise blood pressure. Afferent messages carry signals from various organs and sensory receptors in the body to other organs and, particularly, the brain.

Hypertension, heart failure and chronic kidney disease are a few of many disease states that result from chronic activation of the SNS, especially the renal sympathetic nervous system. Chronic activation of the SNS is a maladaptive response that drives the progression of these disease states. Pharmaceutical management of the renin-angiotensin-aldosterone system (RAAS) has been a longstanding, but somewhat ineffective, approach for reducing over-activity of the SNS.

As mentioned above, the renal sympathetic nervous system has been identified as a major contributor to the complex pathophysiology of hypertension, states of volume overload (such as heart failure), and progressive renal disease, both experimentally and in humans. Studies employing radiotracer dilution methodology to measure overflow of norepinephrine from the kidneys to plasma revealed increased renal norepinephrine (NE) spillover rates in patients with essential hypertension, particularly so in young hypertensive subjects, which in concert with increased NE spillover from the heart, is consistent with the hemodynamic profile typically seen in early hypertension and characterized by an increased heart rate, cardiac output, and renovascular resistance. It is now known that essential hypertension is commonly neurogenic, often accompanied by pronounced sympathetic nervous system overactivity.

Activation of cardiorenal sympathetic nerve activity is even more pronounced in heart failure, as demonstrated by an exaggerated increase of NE overflow from the heart and the kidneys to plasma in this patient group. In line with this notion is the recent demonstration of a strong negative predictive value of renal sympathetic activation on all-cause mortality and heart transplantation in patients with congestive heart failure, which is independent of overall sympathetic activity, glomerular filtration rate, and left ventricular ejection fraction. These findings support the notion that treatment regimens that are designed to reduce renal sympathetic stimulation have the potential to improve survival in patients with heart failure.

Both chronic and end stage renal disease are characterized by heightened sympathetic nervous activation. In patients with end stage renal disease, plasma levels of norepinephrine above the median have been demonstrated to be predictive for both all-cause death and death from cardiovascular disease. This is also true for patients suffering from diabetic or contrast nephropathy. There is compelling evidence suggesting that sensory afferent signals originating front the diseased kidneys are major contributors to initiating and sustaining elevated central sympathetic outflow in this patient group; this facilitates the occurrence of the well-known adverse consequences of chronic sympathetic over activity, such as hypertension, left ventricular hypertrophy, ventricular arrhythmias, sudden cardiac death, insulin resistance, diabetes, and metabolic syndrome.

(i) Renal Sympathetic Efferent Activity

Sympathetic nerves to the kidneys terminate in the blood vessels, the juxtaglomerular apparatus and the renal tubules. Stimulation of the renal sympathetic nerves causes increased renin release, increased sodium ($Na^+$) reabsorption, and a reduction of renal blood flow. These components of the neural regulation of renal function are considerably stimulated in disease states characterized by heightened sympathetic tone and clearly contribute to the rise in blood pressure in hypertensive patients. The reduction of renal blood flow and glomerular filtration rate as a result of renal sympathetic efferent stimulation is likely a cornerstone of the loss of renal function in cardio-renal syndrome, which is renal dysfunction as a progressive complication of chronic heart failure, with a clinical course that typically fluctuates with the patient's clinical status and treatment. Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release) and diuretics (intended to counter the renal sympathetic mediated sodium and water retention). However, the current pharmacologic strategies have significant limitations including limited efficacy, compliance issues, side effects and others.

(ii) Renal Sensory Afferent Nerve Activity

Figure 12:
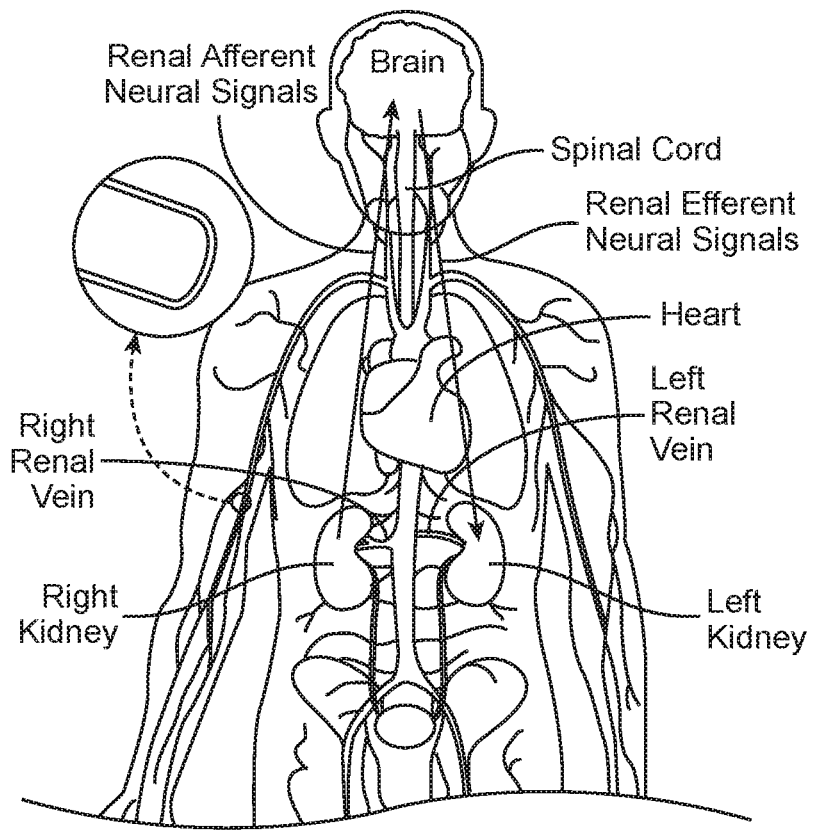
FIGS. 12 and 13 are anatomic and conceptual views, respectively, of a human body depicting neural efferent and afferent communication between the brain and kidneys.
Figure 13:
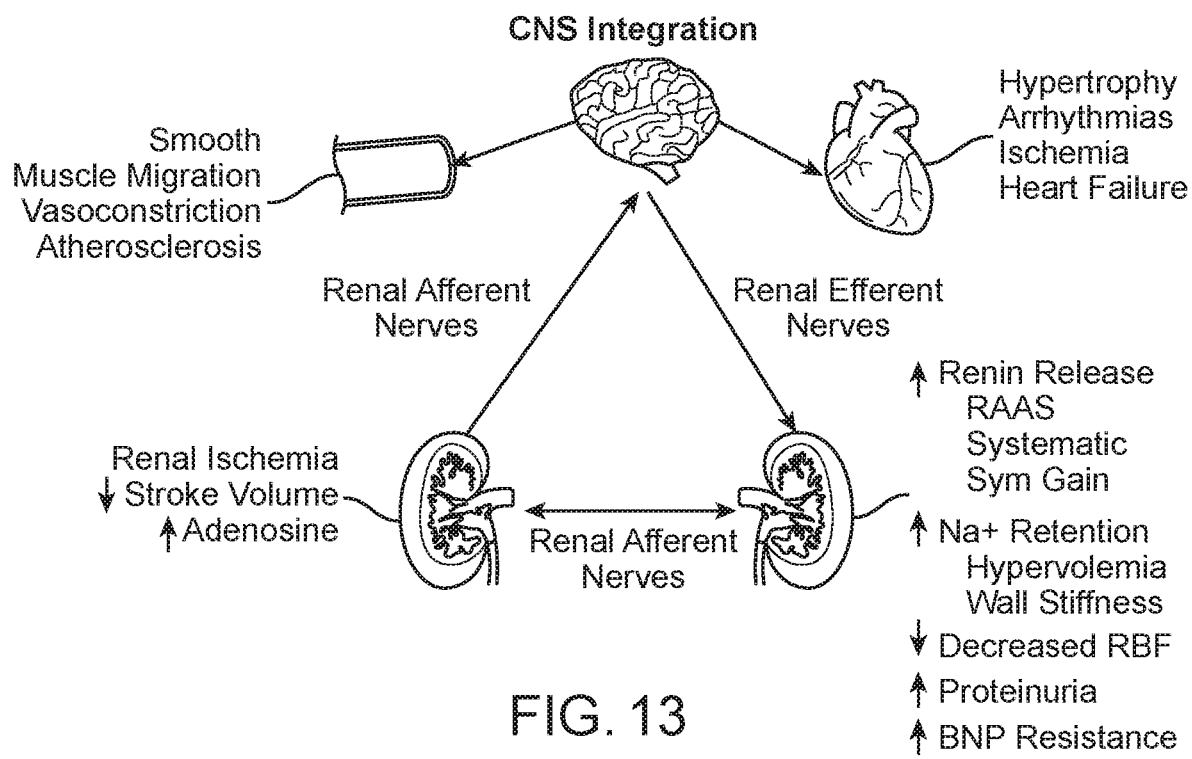

The kidneys communicate with integral structures in the central nervous system via renal sensory afferent nerves. Several forms of "renal injury" may induce activation of sensory afferent signals. For example, renal ischemia, reduction in stroke volume or renal blood flow, or an abundance of adenosine enzyme may trigger activation of afferent neural communication. As shown in FIGS. 12 and 13, this afferent communication might be from the kidney to the brain or might be from one kidney to the other kidney (via the central nervous system). These afferent signals are centrally integrated and may result in increased sympathetic outflow. This sympathetic drive is directed towards the kidneys, thereby activating the RAAS and inducing increased renin secretion, sodium retention, volume retention and vasoconstriction. Central sympathetic over activity also impacts other organs and bodily structures innervated by sympathetic nerves such as the heart and the peripheral vasculature, resulting in the described adverse effects of sympathetic activation, several aspects of which also contribute to the rise in blood pressure.

The physiology therefore suggests that (i) modulation of tissue with efferent sympathetic nerves will reduce inappropriate renin release, salt retention, and reduction of renal blood flow, and that (ii) modulation of tissue with afferent sensory nerves will reduce the systemic contribution to hypertension and other disease states associated with increased central sympathetic tone through its direct effect on the posterior hypothalamus as well as the contralateral kidney. In addition to the central hypotensive effects of afferent renal denervation, a desirable reduction of central sympathetic outflow to various other sympathetically innervated organs such as the heart and the vasculature is anticipated.

B. Additional Clinical Benefits of Renal Denervation

As provided above, renal denervation is likely to be valuable in the treatment of several clinical conditions characterized by increased overall and particularly renal sympathetic activity such as hypertension, metabolic syndrome, insulin resistance, diabetes, left ventricular hypertrophy, chronic end stage renal disease, inappropriate fluid retention in heart failure, cardio-renal syndrome, and sudden death. Since the reduction of afferent neural signals contributes to the systemic reduction of sympathetic tone/drive, renal denervation might also be useful in treating other conditions associated with systemic sympathetic hyperactivity. Accordingly, renal denervation may also benefit other organs and bodily structures innervated by sympathetic nerves, including those identified in FIG. 10. For example, as previously discussed, a reduction in central sympathetic drive may reduce the insulin resistance that afflicts people with metabolic syndrome and Type II diabetics. Additionally, patients with osteoporosis are also sympathetically activated and might also benefit from the down regulation of sympathetic drive that accompanies renal denervation.

C. Achieving Intravascular Access to the Renal Artery

Figure 14:
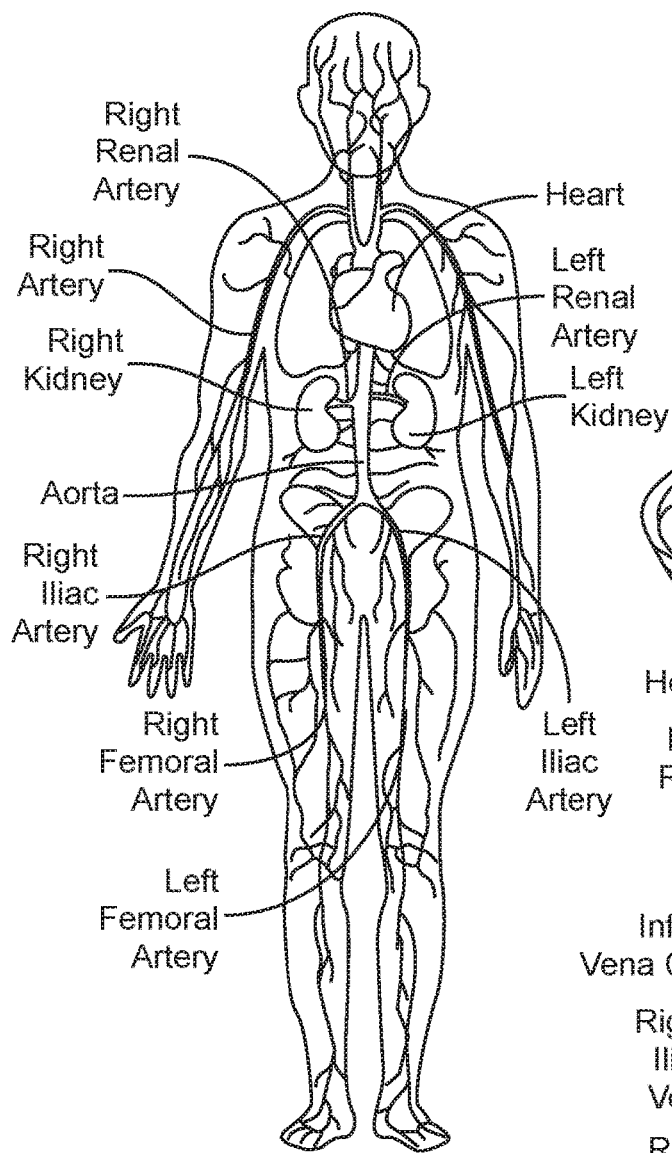
FIGS. 14 and 15 are anatomic views of the arterial vasculature and venous vasculature, respectively, of a human.

In accordance with the present technology, neuromodulation of a left and/or right renal plexus (RP), which is intimately associated with a left and/or right renal artery, may be achieved through intravascular access. As FIG. 14 shows, blood moved by contractions of the heart is conveyed from the left ventricle of the heart by the aorta. The aorta descends through the thorax and branches into the left and right renal arteries. Below the renal arteries, the aorta bifurcates at the left and right iliac arteries. The left and right iliac arteries descend, respectively, through the left and right legs and join the left and right femoral arteries.

Figure 15:
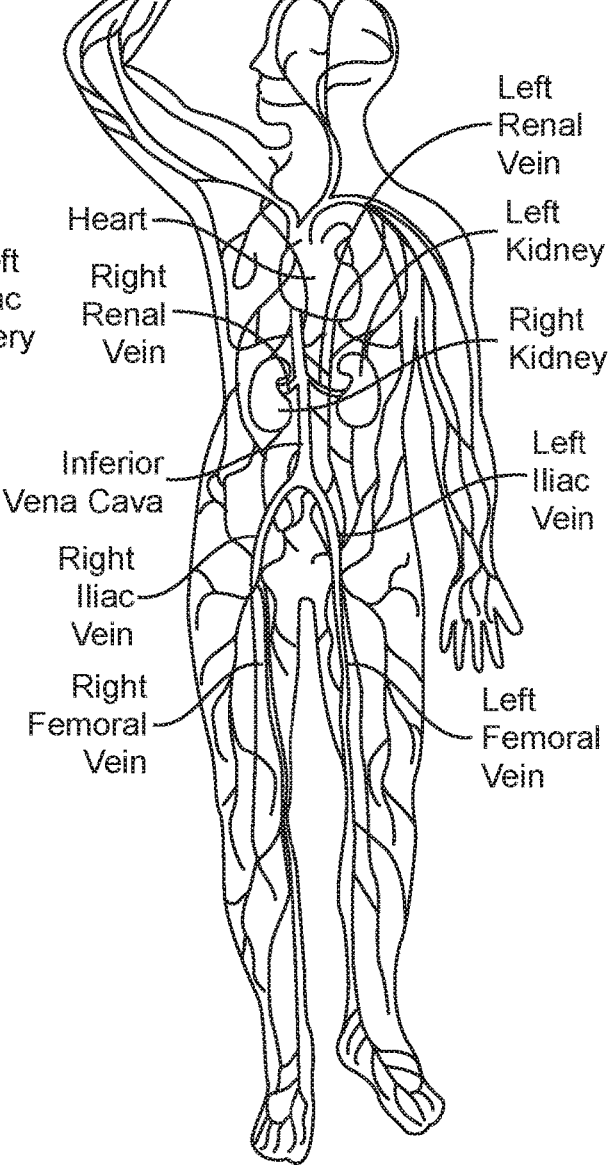

As FIG. 15 shows, the blood collects in veins and returns to the heart, through the femoral veins into the iliac veins and into the inferior vena cava. The inferior vena cava branches into the left and right renal veins. Above the renal veins, the inferior vena cava ascends to convey blood into the right atrium of the heart. From the right atrium, the blood is pumped through the right ventricle into the lungs, where it is oxygenated. From the lungs, the oxygenated blood is conveyed into the left atrium. From the left atrium, the oxygenated blood is conveyed by the left ventricle back to the aorta.

As will be described in greater detail later, the femoral artery may be accessed and cannulated at the base of the femoral triangle just inferior to the midpoint of the inguinal ligament. A catheter may be inserted percutaneously into the femoral artery through this access site, passed through the iliac artery and aorta, and placed into either the left or right renal artery. This comprises an intravascular path that offers minimally invasive access to a respective renal artery and/or other renal blood vessels.

The wrist, upper arm, and shoulder region provide other locations for introduction of catheters into the arterial system. For example, catheterization of either the radial, brachial, or axillary artery may be utilized in select cases. Catheters introduced via these access points may be passed through the subclavian artery on the left side (or via the subclavian and brachiocephalic arteries on the right side), through the aortic arch, down the descending aorta and into the renal arteries using standard angiographic technique.

D. Properties and Characteristics of the Renal Vasculature

Since neuromodulation of a left and/or right renal plexus (RP) may be achieved in accordance with the present technology through intravascular access, properties and characteristics of the renal vasculature may impose constraints upon and/or inform the design of apparatus, systems, and methods for achieving such renal neuromodulation. Some of these properties and characteristics may vary across the patient population and/or within a specific patient across time, as well as in response to disease states, such as hypertension, chronic kidney disease, vascular disease, end-stage renal disease, insulin resistance, diabetes, metabolic syndrome, etc. These properties and characteristics, as explained herein, may have bearing on the efficacy of the procedure and the specific design of the intravascular device. Properties of interest may include, for example, material/mechanical, spatial, fluid dynamic/hemodynamic and/or thermodynamic properties.

As discussed previously, a catheter may be advanced percutaneously into cither the left or right renal artery via a minimally invasive intravascular path. However, minimally invasive renal arterial access may be challenging, for example, because as compared to some other arteries that are routinely accessed using catheters, the renal arteries are often extremely tortuous, may be of relatively small diameter, and/or may be of relatively short length. Furthermore, renal arterial atherosclerosis is common in many patients, particularly those with cardiovascular disease. Renal arterial anatomy also may vary significantly from patient to patient, which further complicates minimally invasive access. Significant inter-patient variation may be seen, for example, in relative tortuosity, diameter, length, and/or atherosclerotic plaque burden, as well as in the take-off angle at which a renal artery branches from the aorta. Apparatus, systems and methods for achieving renal neuromodulation via intravascular access should account for these and other aspects of renal arterial anatomy and its variation across the patient population when minimally invasively accessing a renal artery.

In addition to complicating renal arterial access, specifics of the renal anatomy also complicate establishment of stable contact between neuromodulatory apparatus and a luminal surface or wall of a renal artery. For example, navigation can be impeded by the tight space within a renal artery, as well as tortuosity of the artery. Furthermore, establishing consistent contact is complicated by patient movement, respiration, and/or the cardiac cycle because these factors may cause significant movement of the renal artery relative to the aorta, and the cardiac cycle may transiently distend the renal artery (i.e. cause the wall of the artery to pulse).

Even after accessing a renal artery and facilitating stable contact between neuromodulatory apparatus and a luminal surface of the artery, nerves in and around the adventitia of the artery should be safely modulated via the neuromodulatory apparatus. Effectively applying thermal treatment from within a renal artery is non-trivial given the potential clinical complications associated with such treatment. For example, the intima and media of the renal artery are highly vulnerable to thermal injury. As discussed in greater detail below, the intima-media thickness separating the vessel lumen from its adventitia means that target renal nerves may be multiple millimeters distant from the luminal surface of the artery. Sufficient energy should be delivered to or heat removed from the target renal nerves to modulate the target renal nerves without excessively cooling or heating the vessel wall to the extent that the wall is frozen, desiccated, or otherwise potentially affected to an undesirable extent. A potential clinical complication associated with excessive heating is thrombus formation from coagulating blood flowing through the artery. Given that this thrombus may cause a kidney infarct, thereby causing irreversible damage to the kidney, thermal treatment from within the renal artery should be applied carefully. Accordingly, the complex fluid mechanics and thermodynamic conditions present in the renal artery during treatment, particularly those that may impact heat transfer dynamics at the treatment site, may be important in applying energy (e.g., heating thermal energy) and/or removing heat from the tissue (e.g., cooling thermal conditions) from within the renal artery.

The neuromodulatory apparatus should also be configured to allow for adjustable positioning and repositioning of the energy delivery element within the renal artery since location of treatment may also impact clinical efficacy. For example, it may be tempting to apply a full circumferential treatment from within the renal artery given that the renal nerves may be spaced circumferentially around a renal artery. In some situations, a full-circle lesion likely resulting from a continuous circumferential treatment may be potentially related to renal artery stenosis. Therefore, the formation of more complex lesions along a longitudinal dimension of the renal artery and/or repositioning of the neuromodulatory apparatus to multiple treatment locations may be desirable. It should be noted, however, that a benefit of creating a circumferential ablation may outweigh the potential of renal artery stenosis or the risk may be mitigated with certain embodiments or in certain patients and creating a circumferential ablation could be a goal. Additionally, variable positioning and repositioning of the neuromodulatory apparatus may prove to be useful in circumstances where the renal artery is particularly tortuous or where there are proximal branch vessels off the renal artery main vessel, making treatment in certain locations challenging. Manipulation of a device in a renal artery should also consider mechanical injury imposed by the device on the renal artery. Motion of a device in an artery, for example by inserting, manipulating, negotiating bends and so forth, may contribute to dissection, perforation, denuding intima, or disrupting the interior elastic lamina.

Blood flow through a renal artery may be temporarily occluded for a short time with minimal or no complications. However, occlusion for a significant amount of time should be avoided because to prevent injury to the kidney such as ischemia. It could be beneficial to avoid occlusion all together or, if occlusion is beneficial to the embodiment, to limit the duration of occlusion, for example to 2-5 minutes.

Based on the above described challenges of (1) renal artery intervention, (2) consistent and stable placement of the treatment element against the vessel wall, (3) effective application of treatment across the vessel wall, (4) positioning and potentially repositioning the treatment apparatus to allow for multiple treatment locations, and (5) avoiding or limiting duration of blood flow occlusion, various independent and dependent properties of the renal vasculature that may be of interest include, for example, (a) vessel diameter, vessel length, intima-media thickness, coefficient of friction, and tortuosity; (b) distensibility, stiffness and modulus of elasticity of the vessel wall; (c) peak systolic, end-diastolic blood flow velocity, as well as the mean systolic-diastolic peak blood flow velocity, and mean/max volumetric blood flow rate; (d) specific heat capacity of blood and/or of the vessel wall, thermal conductivity of blood and/or of the vessel wall, and/or thermal connectivity of blood flow past a vessel wall treatment site and/or radiative heat transfer; (e) renal artery motion relative to the aorta induced by respiration, patient movement, and/or blood flow pulsatility; and (f) the take-off angle of a renal artery relative to the aorta. These properties will be discussed in greater detail with respect to the renal arteries. However, dependent on the apparatus, systems and methods utilized to achieve renal neuromodulation, such properties of the renal arteries, also may guide and/or constrain design characteristics.

As noted above, an apparatus positioned within a renal artery should conform to the geometry of the artery. Renal artery vessel diameter, $D_{RA}$, typically is in a range of about 2-10 mm, with most of the patient population having a $D_{RA}$ of about 4 mm to about 8 mm and an average of about 6 mm. Renal artery vessel length, $L_{RA}$, between its ostium at the aorta/renal artery juncture and its distal branchings, generally is in a range of about 5-70 mm, and a significant portion of the patient population is in a range of about 20-50 mm. Since the target renal plexus is embedded within the adventitia of the renal artery, the composite Intima-Media Thickness, IMT, (i.e., the radial outward distance from the artery's luminal surface to the adventitia containing target neural structures) also is notable and generally is in a range of about 0.5-2.5 mm, with an average of about 1.5 mm. Although a certain depth of treatment is important to reach the target neural fibers, the treatment should not be too deep (e.g., >5 mm from inner wall of the renal artery) to avoid non-target tissue and anatomical structures such as the renal vein.

An additional property of the renal artery that may be of interest is the degree of renal motion relative to the aorta induced by respiration and/or blood flow pulsatility. A patient's kidney, which is located at the distal end of the renal artery, may move as much as 4" cranially with respiratory excursion. This may impart significant motion to the renal artery connecting the aorta and the kidney, thereby requiring from the neuromodulatory apparatus a unique balance of stiffness and flexibility to maintain contact between the energy delivery element and the vessel wall during cycles of respiration. Furthermore, the take-off angle between the renal artery and the aorta may vary significantly between patients, and also may vary dynamically within a patient, e.g., due to kidney motion. The take-off angle generally may be in a range of about 30°-135°.

VIII. EXAMPLES

1. A system, comprising:
   a neuromodulation catheter including—
      an elongated shaft having a distal portion configured to be intravascularly positioned at a target site within a blood vessel of a human patient; and a plurality of electrodes spaced apart along the distal portion of the shaft, wherein the electrodes are configured to deliver neuromodulation energy to target nerves at or adjacent to the target site;

an optical magnetic sensor configured to detect measurements of a magnetic field generated by the target nerves; and a controller configured to be communicatively coupled to the optical magnetic sensor, wherein the controller is further configured to— receive a baseline measurement of the magnetic field generated by the target nerves from the optical magnetic sensor before delivery of neuromodulation energy;

after neuromodulation energy is delivered at the target site via the electrodes, receive a post-neuromodulation measurement of the magnetic field generated by the target nerves from the optical magnetic sensor; and compare the baseline measurement to the post-neuromodulation measurement.

2. The system of example 1 wherein, based on the comparison of the baseline measurement to the post-neuromodulation measurement, the controller is configured to determine a percentage that the target nerves were ablated by the delivered neuromodulation energy.

3. The system of example 1 or example 2 wherein, based on at least one of the baseline measurement and the post-neuromodulation measurement, the controller is configured to determine a location of ablation at one or more of the target nerves.

4. The system of any one of examples 1-3 wherein the optical magnetic sensor is optically coupled to an optical source, wherein the controller is communicatively coupled to the optical source, and wherein the controller is configured to cause the optical source to generate an optical signal and transmit the optical signal to the optical magnetic sensor.

5. The system of example 4 wherein the optical magnetic sensor includes a chamber and a detection element, wherein the chamber includes gaseous cesium, and wherein the detection element is configured to detect a property of the optical signal after it passes through the chamber.

6. The system of any one of examples 1-5 further comprising means for generating a variable magnetic field at or near the target nerves.

7. The system of example 6 wherein the variable magnetic field is configured to amplify and/or enhance the magnetic field generated by the target nerves.

8. The system of any one of examples 1-7 wherein the neuromodulation catheter includes a plurality of electromagnets, wherein the controller is communicatively coupled to the electromagnets, and wherein the controller is configured to cause the electromagnets to generate a variable magnetic field at or near the target nerves.

9. The system of any one of examples 1-9 wherein the optical magnetic sensor is intravascularly positioned within the blood vessel.

10. The system of example 9 wherein the optical magnetic sensor is coupled to or positioned within the neuromodulation catheter.

11. The system of example 9, further comprising an optical catheter configured to be intravascularly positioned near the target site within the blood vessel, and wherein the optical magnetic sensor is coupled to the optical catheter.

12. The system of any one of examples 1-11, further comprising an energy generator coupled to the plurality of electrodes, wherein the controller is communicatively coupled to the energy generator and the electrodes, and wherein the controller is configured to cause the energy generator to deliver the neuromodulation energy via the electrodes.

13. A method, comprising:

positioning a neuromodulation catheter having one or more electrodes at a target site within a renal blood vessel of a human patient;

detecting a baseline measurement of a magnetic field generated by target renal nerves located at or adjacent to the target site within the renal blood vessel;

delivering neuromodulation energy to the target renal nerves via the one or more electrodes;

detecting a post-neuromodulation measurement of the magnetic field generated by the target renal nerves; and comparing the post-neuromodulation measurement to the baseline measurement.

14. The method of example 13 wherein detecting the baseline measurement and the post-neuromodulation measurement includes detecting the measurements via an optical magnetic sensor positioned intravascularly near the target site.

15. The method of example 13 or example 14, further comprising determining a percentage that the target renal nerves were ablated by the delivered neuromodulation energy based on the comparison of the post-neuromodulation measurement to the baseline measurement.

16. The method of example 15, further comprising adjusting one or more parameters of neuromodulation energy to be subsequently delivered to the target renal nerves based on the determined percentage.

17. The method of any one of examples 13-16, further comprising generating a variable magnetic field at or near the target renal nerves.

18. A system, comprising:

a neuromodulation catheter including— an elongated shaft having a distal portion configured to be intravascularly positioned at a target site within a blood vessel of a human patient; and a plurality of electrodes spaced apart along the distal portion of the shaft, wherein the electrodes are configured to deliver neuromodulation energy to target nerves at or adjacent to the target site;

an optical magnetic sensor configured to detect measurements of a magnetic field generated by the target nerves; and a controller configured to be communicatively coupled to the optical magnetic sensor, wherein the controller is further configured to— receive a measurement of the magnetic field generated by the target nerves from the optical magnetic sensor; and determine a location of one or more of the target nerves.

19. The system of example 18 wherein the controller is further configured to— after neuromodulation energy is delivered at the target site via the electrodes, receive a measurement of the magnetic field generated by the target nerves from the optical magnetic sensor; and based on the measurement, determine a location of ablation at one or more of the target nerves.

20. The system of example 18 or example 19, further comprising:
means for generating a variable magnetic field at or near the target nerves, wherein the variable magnetic field is configured to amplify and/or enhance the magnetic field generated by the target nerves; and
an energy generator coupled to the plurality of electrodes, wherein the controller is communicatively coupled to the energy generator and the electrodes, and wherein the controller is configured to cause the energy generator to deliver the neuromodulation energy via the electrodes.

21. A system, comprising:
a neuromodulation catheter including—
an elongated shaft having a distal portion configured to be intravascularly positioned at a target site within a blood vessel of a human patient; and
a plurality of electrodes spaced apart along the distal portion of the shaft, wherein the electrodes are configured to deliver neuromodulation energy to target nerves at or adjacent to the target site;
an optical magnetic sensor configured to detect measurements of a magnetic field generated by the target nerves; and
a controller configured to be communicatively coupled to the optical magnetic sensor, wherein the controller is further configured to—
after neuromodulation energy is delivered at the target site via the electrodes, receive a measurement of the magnetic field generated by the target nerves from the optical magnetic sensor; and
based on the measurement, determine a location of ablation at one or more of the target nerves.

IX. CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. Moreover, the various embodiments described herein may also be combined to provide further embodiments. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment.

Certain aspects of the present technology may take the form of computer-executable instructions, including routines executed by a controller or other data processor. In some embodiments, a controller or other data processor is specifically programmed, configured, and/or constructed to perform one or more of these computer-executable instructions. Furthermore, some aspects of the present technology may take the form of data (e.g., non-transitory data) stored or distributed on computer-readable media, including magnetic or optically readable and/or removable computer discs as well as media distributed electronically over networks.

Accordingly, data structures and transmissions of data particular to aspects of the present technology are encompassed within the scope of the present technology. The present technology also encompasses methods of both programming computer-readable media to perform particular steps and executing the steps.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Where the context permits, singular or plural terms may also include the plural or singular term, respectively. Additionally, the term "comprising" is used throughout to mean including at least the recited feature(s) such that any greater number of the same feature and/or additional types of other features are not precluded. Directional terms, such as "upper," "lower," "front," "back," "vertical," and "horizontal," may be used herein to express and clarify the relationship between various elements. It should be understood that such terms do not denote absolute orientation. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A system comprising:
an optical magnetic sensor configured to generate a signal indicative of a measurement of a magnetic field generated by a target nerve within a patient; and
a controller configured to:
determine a baseline measurement of the magnetic field generated by the target nerve based on the signal generated by optical magnetic sensor before delivery of neuromodulation treatment to a target site within the patient, wherein the baseline measurement includes at least one of a magnitude of the magnetic field, a distance from the optical magnetic sensor to the target nerve, a magnitude of an impulse of the target nerve or a temporal extent of the impulse of the target nerve;
after the neuromodulation treatment is delivered at the target site, determine a post-neuromodulation measurement of the magnetic field generated by the target nerve based on the signal generated by the optical magnetic sensor, wherein the post-neuromodulation measurement includes the at least one of the magnitude of the magnetic field, the distance from the optical magnetic sensor to the target nerve, the magnitude of the impulse of the target nerve or the temporal extent of the impulse of the target nerve;
compare the baseline measurement to the post-neuromodulation measurement; and
based on the comparison of the baseline measurement to the post-neuromodulation measurement, determine a percentage that the target nerve was ablated by the delivered neuromodulation treatment.

2. The system of claim 1, wherein the neuromodulation treatment is configured to ablate the target nerve.

3. The system of claim 1, wherein the neuromodulation treatment is configured to modulate activity of the target nerve via electrically-induced ablation.

4. The system of claim 1, wherein the neuromodulation treatment is configured to modulate activity of the target nerve via thermally-induced ablation.

5. The system of claim 1, wherein the neuromodulation treatment is configured to modulate activity of the target nerve via chemically-induced ablation.

6. The system of claim 1, wherein the neuromodulation treatment comprises at least one of delivery of radiofrequency energy, delivery of electrical energy, delivery of microwave energy, delivery of optical energy, delivery of ultrasound energy, delivery of direct heat energy, delivery of radiation, delivery of cryogenic cooling, or delivery of a chemical.

7. The system of claim 1, further comprising:
a catheter; and
a console configured to deliver the neuromodulation treatment to the target site, wherein the controller is configured to control the console to adjust one or more parameters of the neuromodulation treatment to be subsequently delivered to the target nerve based on the percentage.

8. The system of claim 1, wherein the target nerve comprises a plurality of target nerves, and wherein the baseline measurement includes at least one of the distance from the optical magnetic sensor to one or more of the target nerves of the plurality of target nerves, a magnitude of impulses of the plurality of target nerves or a temporal extent of the impulses of the plurality of target nerves.

9. The system of claim 1, further comprising an optical source optically coupled to the optical magnetic sensor, wherein the controller is configured to cause the optical source to generate an optical signal and transmit the optical signal to the optical magnetic sensor.

10. The system of claim 1, wherein the optical magnetic sensor includes:
a chamber; and
a detection element configured to detect a property of the optical signal after it passes through the chamber.

11. The system of claim 1, further comprising a magnet assembly configured to generate a variable magnetic field at or near the target nerve, wherein the variable magnetic field is configured to amplify or enhance the magnetic field generated by the target nerve.

12. The system of claim 1, wherein the optical magnetic sensor is configured to be intravascularly positioned within a blood vessel.

13. A system comprising:
an optical magnetic sensor configured to measure a magnetic field generated by target nerves at or adjacent to a target site within a patient; and
a controller configured to:
receive a first measurement of the magnetic field generated by the target nerves from the optical magnetic sensor before delivery of neuromodulation therapy to the target site, wherein the first measurement includes at least one of a magnitude of the magnetic field, a distance from the optical magnetic sensor to one or more of the target nerves, a magnitude of impulses of the target nerves, a magnitude of impulses of the target nerves, or a temporal extent of the impulses of the target nerves;
determine a location of one or more of the target nerves based on the measurement;
after the neuromodulation energy is delivered at the target site, receive a second measurement of the magnetic field generated by the target nerves from the optical magnetic sensor, wherein the second measurement includes the at least one of the magnitude of the magnetic field, the distance from the optical magnetic sensor to the one or more of the target nerves, the magnitude of the impulses of the target nerves or the temporal extent of the impulses of the target nerves;
compare the first measurement to the second measurement; and
based on the comparison of the first measurement to the second measurement, determine a percentage that the target nerves were ablated by the delivered neuromodulation therapy.

14. The system of claim 13, wherein the neuromodulation therapy comprises at least one of delivery of radiofrequency energy, delivery of electrical energy, delivery of microwave energy, delivery of optical energy, delivery of ultrasound energy, delivery of direct heat energy, delivery of radiation, delivery of cryogenic cooling, or delivery of a chemical.

15. The system of claim 13, further comprising:
a magnet assembly configured to generate a variable magnetic field at or near the target nerves, wherein the variable magnetic field is configured to at least one of amplify or enhance the magnetic field generated by the target nerves; and
a catheter; and
a console, wherein the controller is configured to cause the console to deliver the neuromodulation therapy to the target site via the catheter.

16. The system of claim 15, wherein the controller is configured to control the console to adjust one or more parameters of neuromodulation therapy to be subsequently delivered to the target nerves based on the percentage.

17. A method comprising:
receiving, by a controller and from an optical magnetic sensor, a baseline measurement of a magnetic field generated by target nerves of a patient before delivery of neuromodulation treatment to a target site within the patient, wherein the baseline measurement includes at least one of a magnitude of the magnetic field, a distance from the optical magnetic sensor to one or more of the target nerves, a magnitude of impulses of the target nerves or a temporal extent of the impulses of the target nerves;
delivering the neuromodulation treatment to the target nerves;
after delivering the neuromodulation treatment, receiving, by the controller, a post-neuromodulation measurement of the magnetic field generated by the target nerves from the optical magnetic sensor, wherein the post-neuromodulation measurement includes the at least one of the magnitude of the magnetic field, the distance from the optical magnetic sensor to one or more of the target nerves, the magnitude of impulses of the target nerves, or the temporal extent of the impulses of the target nerves;
comparing, by the controller, the post-neuromodulation measurement to the baseline measurement; and
based on the comparison of the baseline measurement to the post-neuromodulation measurement, determining, by the controller, a percentage that the target nerves were ablated by delivering the neuromodulation energy.

18. The method of claim 17, further comprising adjusting one or more parameters of neuromodulation treatment to be subsequently delivered to the target nerves based on the determined percentage.

19. The method of claim 17, further comprising generating a variable magnetic field at or near the target nerves.

20. The method of claim 17, wherein delivering the neuromodulation treatment to the target nerves comprises modulating activity of the target nerves via at least one of electrically-induced ablation, thermally-induced ablation, or chemically-induced ablation.

\* \* \* \* \*